United States Patent
Lofgren et al.

(10) Patent No.: US 11,445,023 B2
(45) Date of Patent: Sep. 13, 2022

(54) COMPUTING NETWORKS AND SYSTEMS FOR IMPLEMENTING A DATA CLOUD

(71) Applicant: Veeva Systems Inc., Pleasanton, CA (US)

(72) Inventors: Lindsey Lofgren, New York, NY (US); Gary Abramsky, New York, NY (US); Leanora Drumm, New York, NY (US)

(73) Assignee: Veeva Systems Inc., Pleasanton, CA (US)

(*) Notice: Subject to any disclaimer, the term of this patent is extended or adjusted under 35 U.S.C. 154(b) by 0 days.

(21) Appl. No.: 17/125,926

(22) Filed: Dec. 17, 2020

(65) Prior Publication Data

US 2022/0201074 A1    Jun. 23, 2022

(51) Int. Cl.
*H04L 67/1097* (2022.01)
*G06F 16/2458* (2019.01)
*G06F 3/0482* (2013.01)

(52) U.S. Cl.
CPC ...... *H04L 67/1097* (2013.01); *G06F 16/2477* (2019.01); *G06F 3/0482* (2013.01)

(58) Field of Classification Search
CPC . H04L 67/1097; G06F 16/2477; G06F 3/0482
USPC .......................................................... 709/201
See application file for complete search history.

(56) References Cited

U.S. PATENT DOCUMENTS

| | | | |
|---|---|---|---|
| 11,283,888 B2 * | 3/2022 | Joseph | G06F 16/22 |
| 2020/0120050 A1 * | 4/2020 | Jung | H04L 51/04 |
| 2021/0279304 A1 * | 9/2021 | Kidd | G06F 21/128 |

* cited by examiner

*Primary Examiner* — Frantz B Jean
(74) *Attorney, Agent, or Firm* — Baker & McKenzie LLP

(57) ABSTRACT

Systems and methods are provided for managing and accessing data using one or more data cloud servers. An exemplary method includes: retrieving from one or more external sources, output data; receiving a first instruction from a user to provide access to the output data to a first set of one or more recipient systems; providing the first set of one or more recipient systems with access to the output data; receiving a second instruction from the first set of the one or more recipient systems to provide access to the output data to a second set of the one or more recipient systems; providing the second set of the one or more recipient systems with access to the output data.

20 Claims, 23 Drawing Sheets

| ▽ Data Cloud | | | | | | 418 — Pull Data | Job Manager — 420 | Ⓖ |
|---|---|---|---|---|---|---|---|---|
| Job Manager - Submitted Jobs | | | | | | | | |
| ● Jobs ○ Drafts | | | | | | | | |
| ▼ Job ID | Query | Submitted | Product | Initiated by | Cadence | Status | Completed | TPA | Duplicate |
| 12345 | Cholecap | 8/15/20 - 12:00 | Patient | gsmith@m1.com | One time | ⊙ Processing | NA | NA | Duplicate |
| 1235 | Somatuline Research 1 | 8/15/20 - 12:00 | Patient | gsmith@m1.com | One time | ⊙ Complete | 8/25/20 - 12:00 | Share | Duplicate |
| 2233 | Somatuline Research | 8/15/20 - 12:00 | Patient | gsmith@m1.com | One time | ⊙ Complete | 8/25/20 - 12:00 | Share | Duplicate |

Data Cloud     418—Pull Data     Job Manager—420

Job Manager

🔍 Job name, user, product, market definition not submitted   submitted

Sort by 1202
[ User - Status ▾ ]

1-8 of 27   < >

| Job Name | Product | Initiated by | Date Submitted | Status | Cadence |
|---|---|---|---|---|---|
| HR + HER2- Metastatic Breast Cancer Launch Analysis System | Patient | gsmith@m1.com | 6/6/20 | Active Stream — 1204 | ⊘ Daily Stop |
| Shared with: N/A (one time pulls only)   Expires: N/A | | | | TPA Record: N/A | |
| HR + HER2- Metastatic Breast Cancer   1210 | Patient | gsmith@m1.com | 6/6/20 | Pull Complete — 1206 | One time re-pull |
| Shared with: (M)(J) John Doe, Accenture | | | | TPA Record: HR + HER2- Metatasti... | |
| HR + HER2- Metastatic Breast Cancer Launch | Patient | gsmith@m1.com | 6/6/20 | Pull Complete — 1208 | One time |

Data Cloud

Job Manager

🔍 Job name, user, product, market definition — 1512

Sort by
[Date Shared ▲▼] — 1514

1502    1504    1506    1501 1508    1510    0-1 of 1 ‹ ›

| Job Name | Product | Shared by | Date Shared | Expires On |
|---|---|---|---|---|
| HR + HER2- Metastatic Breast Cancer Launch Analysis One Time | Patient | Ⓖ Gary Smith M1 | 6/6/20 | 9/6/20 |

NEW — 1516

Accept  Decline

| HR + HER2- Metastatic Breast Cancer | Patient | Ⓖ Gary Smith M1 | 6/6/20 | 9/6/20 |

Step 3 - Select data attributes [Skip]

1702 — Select by use case 1704
- [Patient Journey] 1722
- [Targeting]
- [Market Access] 1706 / 1724
- [HEOR] 1708
- [Segmentation] 1710 / 1726
- [Medical Affairs] 1712 / 1728

○ Select All — 1714
○ Select None — 1716
⦿ Only Show Selected — 1718

| Data File 1720 | Select All Attributes | Category | Attribute | Example Data 1742 |
|---|---|---|---|---|
| | ☑ | Core — 1736a | 10/10 attributes selected | See Individual Attributes > |
| Claims/Rx 1730 | ☐ | Transaction Details — 1736b | 0/8 attributes selected | > |
| | ☐ | Patient — 1736c | 0/4 attributes selected | > |
| | ☐ | HCP — 1736d | 0/8 attributes selected | > |
| | ☐ | Payer — 1736e | 0/8 attributes selected | > |
| | ☐ | Analytics Attribute — 1736f | 0/4 attributes selected | > |
| Rx Only 1732 | ☑ | Rx Core — 1738a | 5/5 attributes selected | > |
| | ☐ | Product — 1738b | 0/8 attributes selected | > |
| | ☐ | Rx Payer — 1738c | 0/8 attributes selected | > |
| Claims Only 1734 | ☑ | MC Core — 1740a | 10/10 attributes selected | > |
| | ☐ | Diagnosis — 1740b | 0/8 attributes selected | > |
| | ☐ | Procedure — 1740c | 0/8 attributes selected | > |

[Done] — 1744

Data Cloud — Home · Pull Data · Job Manager

◯ Make home ......... Job Manager

1802

| Job Name — 1804 | Target File Name — 1806 | Data Product — 1808 | Initiated — 1810 | Completed — 1812 | Pull Status |
|---|---|---|---|---|---|
| HR+ HER2- Metastatic Breast Cancer Launch Analysis | HR+_HER2_Metastatic_Breast_Cancer_Launch_Analysis | Crossix Patient | 6/8/2020 | 6/9/2020 | One Time |

1-10 of 16 < >

MARKET DEFINITION — 1814 — 1818 [Edit] — 1832a

Market Definition: HR+, HER2- Metastatic Breast Cancer — 1832b

Products: Patient: Med Claims, Rx Claims — 1832c

Timeframe: Last Full 6 Months — 1832d

Patient Data: Include all longitudinal patient data

LONGITUDINAL PATIENT DATA — 1816 — 1834a [Edit] — 1820a

Filter: Include all patient data

Timeframe: Last Full 2 Years — 1834b [Edit] — 1820b

ATTRIBUTES — 1817

Preview — 1824 [Edit] — 1822

Download to — 1840

● My Computer  ○ sFTP  ○ s3

[Continue]

1826 — [Download Data]    [Schedule a Data Stream] — 1828    [Edit Request] — 1830

| ☆ | Cholecap: Commercial Reporting | Crossix Prescriber | 5/28/2020 | 5/29/2020 | Weekly ⌄ |
| ☆ | Cholecap: Account Performance Reporting | Crossix Prescriber | 5/27/2020 | 5/28/2020 | Weekly ⌄ |

1800

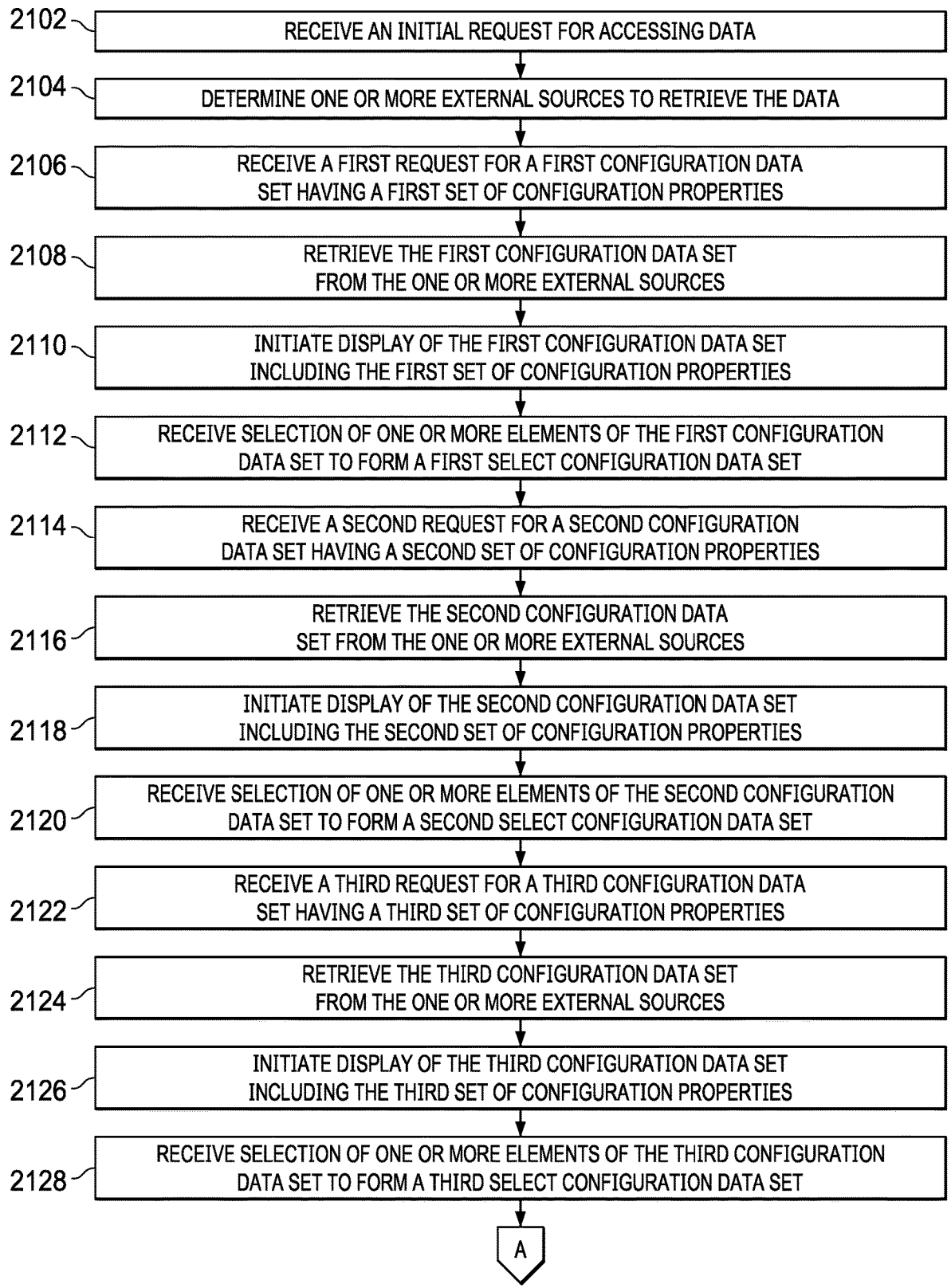

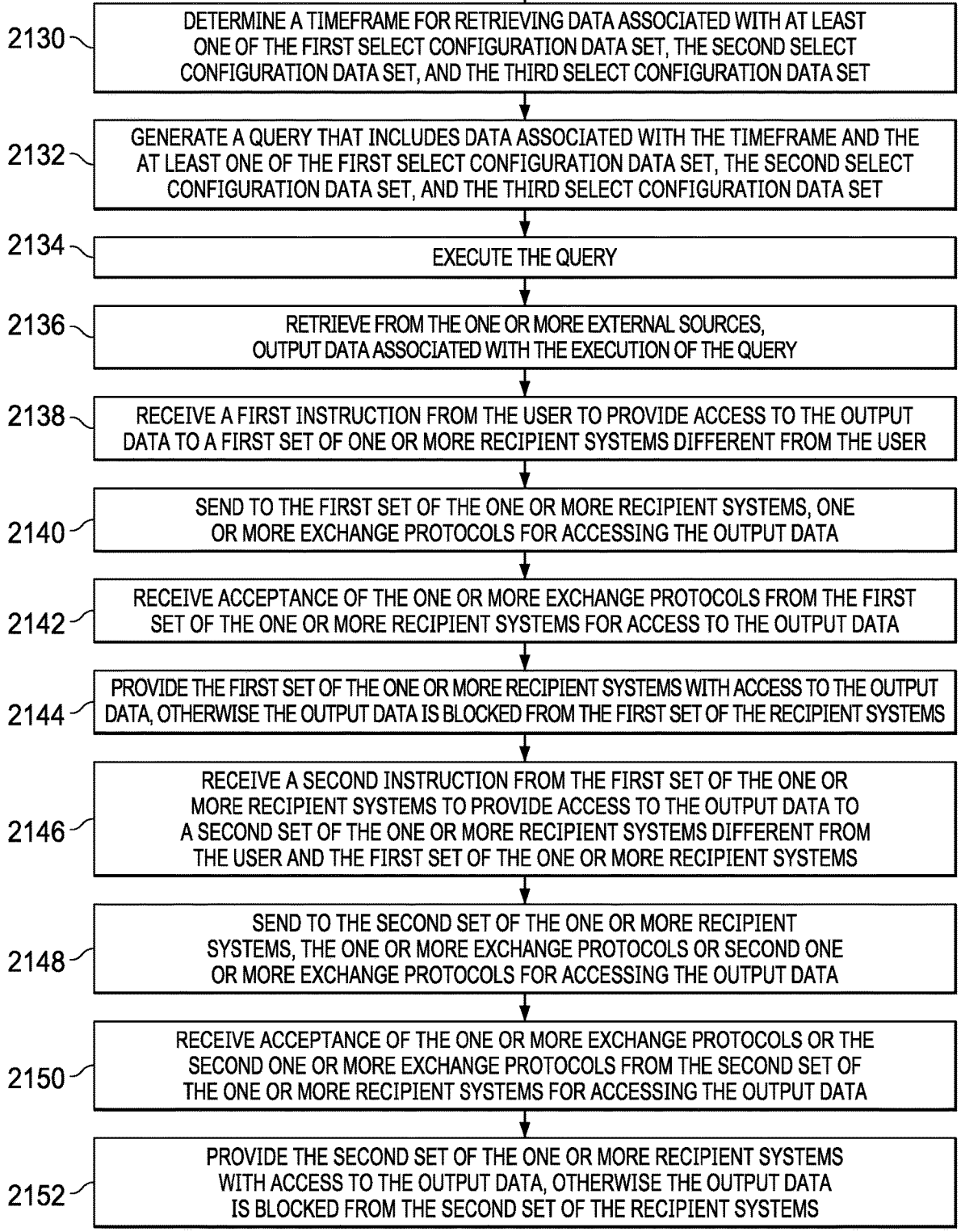

COMPUTING NETWORKS AND SYSTEMS FOR IMPLEMENTING A DATA CLOUD

TECHNICAL FIELD

The present disclosure relates to methods and systems for accessing and sharing data using complex computing networks and systems for implementing a data cloud.

BACKGROUND

Researchers, scientists, industry players, academics, government regulators, and other stakeholders are increasingly in need of data that is accessible, easy to interpret, analyze, and/or visualize.

SUMMARY

According to one aspect of the subject matter described in this disclosure, a method for managing and accessing data using one or more data cloud servers is provided. The method includes the following: receiving, using one or more computing device processors, an initial request for accessing data; determining, using the one or more computing device processors, one or more external sources to retrieve the data; receiving, using the one or more computing device processors, a first request for a first configuration data set having a first set of configuration properties; retrieving, using the one or more computing device processors, the first configuration data set from the one or more external sources; initiating display of, using the one or more computing device processors, the first configuration data set including the first set of configuration properties; receiving selection of, using the one or more computing device processors, one or more elements of the first configuration data set to form a first select configuration data set; receiving, using the one or more computing device processors, a second request for a second configuration data set having a second set of configuration properties; retrieving, using the one or more computing device processors, the second configuration data set from the one or more external sources; initiating display of, using the one or more computing device processors, the second configuration data set including the second set of configuration properties; receiving selection of, using the one or more computing device processors, one or more elements of the second configuration data set to form a second select configuration data set; receiving, using the one or more computing device processors, a third request for a third configuration data set having a third set of configuration properties; retrieving, using the one or more computing device processors, the third configuration data set from the one or more external sources; initiating display of, using the one or more computing device processors, the third configuration data set including the third set of configuration properties; receiving selection of, using the one or more computing device processors, one or more elements of the third configuration data set to form a third select configuration data set; determining, using the one or more computing device processors, a timeframe for retrieving data associated with at least one of the first select configuration data set, the second select configuration data set, and the third select configuration data set; generating, using the one or more computing device processors, a query based on data associated with the timeframe, the at least one of the first select configuration data set, the second select configuration data set, and the third select configuration data set, or other data related to the at least one of the first select configuration data set, the second select configuration data set, and the third select configuration data set; executing, using the one or more computing device processors, the query according to a cadence; retrieving, using the one or more computing device processors, from the one or more external sources, output data, using the one or more computing device processors, a first instruction from the user to provide access to the output data to a first set of one or more recipient systems; in response to receiving the first instruction from the user to provide access to the output data, sending, using the one or more computing device processors, to the first set of the one or more recipient systems, one or more exchange protocols for accessing the output data; receiving, using the one or more computing device processors, acceptance of the one or more exchange protocols from the first set of the one or more recipient systems for access to the output data; in response to receiving the acceptance of the one or more exchange protocols from the first set of the one or more recipient systems, providing, using the one or more computing device processors, the first set of the one or more recipient systems with access to the output data, otherwise the output data is blocked from the first set of the recipient systems; receiving, using the one or more computing device processors, a second instruction from the first set of the one or more recipient systems to provide access to the output data to a second set of the one or more recipient systems; in response to receiving the second instruction from the first set of the one or more recipient systems to provide access to the output data, sending, using the one or more computing device processors, to the second set of the one or more recipient systems, the one or more exchange protocols or second one or more exchange protocols for accessing the output data; receiving, using the one or more computing device processors, acceptance of the one or more exchange protocols or the second one or more exchange protocols from the second set of the one or more recipient systems for accessing the output data; and in response to receiving the acceptance of the one or more exchange protocols or the second one or more exchange protocols from the second set of the one or more recipient systems, providing, using the one or more computing device processors, the second set of the one or more recipient systems with access to the output data, otherwise the output data is blocked from the second set of the recipient systems.

According to another aspect of the subject matter described in this disclosure, a system for managing and accessing data using one or more data cloud servers is provided. The system includes one or more computing device processors. One or more computing device memories are coupled to the one or more computing device processors. The one or more computing device memories store instructions executed by the one or more computing device processors, the instructions are configured to: receive an initial request for accessing data; determine one or more external sources to retrieve the data; receive a first request for a first configuration data set having a first set of configuration properties; retrieve the first configuration data set from the one or more external sources; initiate display of the first configuration data set including the first set of configuration properties; receive selection of one or more elements of the first configuration data set to form a first select configuration data set; receive a second request for a second configuration data set having a second set of configuration properties; retrieve the second configuration data set from the one or more external sources; initiate display of the second configuration data set including the second set of configuration properties; receive selection of one or more elements of the second configuration data set to form a second select configuration data set; receive a third request for a third configuration data set having a third set of configuration properties; retrieve the third configuration data set from the one or more external sources; initiate display of the third configuration data set including the third set of configuration properties; receive selection of one or more elements of the third configuration data set to form a third select configuration data set; determine a timeframe for retrieving data associated with at least one of the first select configuration data set, the second select configuration data set, and the third select configuration data set; generate a query based data associated with the timeframe, the at least one of the first select configuration data set, the second select configuration data set, and the third select configuration data set, or other data related to the at least one of the first select configuration data set, the second select configuration data set, and the third select configuration data set; execute the query according to a cadence; retrieve from the one or more external sources, output data; receive a first instruction from the user to provide access to the output data to a first set of one or more recipient systems; in response to receiving the first instruction from the user to provide access to the output data, send to the first set of the one or more recipient systems, one or more exchange protocols for accessing the output data; receive acceptance of the one or more exchange protocols from the first set of the one or more recipient systems for access to the output data; in response to receiving the acceptance of the one or more exchange protocols from the first set of the one or more recipient systems, provide the first set of the one or more recipient systems with access to the output data, otherwise the output data is blocked from the first set of the recipient systems; receive a second instruction from the first set of the one or more recipient systems to provide access to the output data to a second set of the one or more recipient systems; in response to receiving the second instruction from the first set of the one or more recipient systems to provide access to the output data, send to the second set of the one or more recipient systems, the one or more exchange protocols or second one or more exchange protocols for accessing the output data; receive acceptance of the one or more exchange protocols or the second one or more exchange protocols from the second set of the one or more recipient systems for accessing the output data; and in response to receiving the acceptance of the one or more exchange protocols or the second one or more exchange protocols from the second set of the one or more recipient systems, provide the second set of the one or more recipient systems with access to the output data, otherwise the output data is blocked from the second set of the recipient systems.

According to another aspect of the subject matter described in this disclosure, a method for managing and accessing data using one or more data cloud servers is provided. The method includes the following: receiving, using one or more computing device processors, a first request for accessing data; determining, using the one or more computing device processors, one or more external sources to retrieve the data; retrieving, using the one or more computing device processors, at least first configuration data set from the one or more external sources, wherein the first configuration data set has at least a first set of configuration properties; initiating display of, using the one or more computing device processors, the at least first configuration data set including the at least first set of configuration properties; receiving selection of, using the one or more computing device processors, one or more elements of the at least first configuration data set to form at least a first select configuration data set; determining, using the one or more computing device processors, a timeframe for retrieving data associated with the at least first select configuration data set; generating, using the one or more computing device processors, a query based on data associated with the timeframe, the at least first select configuration data set, or other data related to the at least first select configuration data set; executing, using the one or more computing device processors, the query according to a cadence; retrieving, using the one or more computing device processors, from the one or more external sources, output data; receiving, using the one or more computing device processors, a first instruction from the user to provide access to the output data to a first set of one or more recipient systems; in response to receiving the first instruction from the user to provide access to the output data, sending, using the one or more computing device processors, to the first set of the one or more recipient systems, one or more exchange protocols for accessing the output data; receiving, using the one or more computing device processors, acceptance of the one or more exchange protocols from the first set of the one or more recipient systems for access to the output data; in response to receiving the acceptance of the one or more exchange protocols from the first set of the one or more recipient systems, providing, using the one or more computing device processors, the first set of the one or more recipient systems with access to the output data; receiving, using the one or more computing device processors, a second instruction from the first set of the one or more recipient systems to provide access to the output data to a second set of the one or more recipient systems; in response to receiving the second instruction from the first set of the one or more recipient systems to provide access to the output data, sending, using the one or more computing device processors, to the second set of the one or more recipient systems, the one or more exchange protocols or second one or more exchange protocols for accessing the output data; receiving, using the one or more computing device processors, acceptance of the one or more exchange protocols or the second one or more exchange protocols from the second set of the one or more recipient systems for accessing the output data; and in response to receiving the acceptance of the one or more exchange protocols or the second one or more exchange protocols from the second set of the one or more recipient systems, providing, using the one or more computing device processors, the second set of the one or more recipient systems with access to the output data.

BRIEF DESCRIPTION OF THE DRAWINGS

The disclosure is illustrated by way of example, and not by way of limitation in the figures of the accompanying drawings in which like reference numerals are used to refer to similar elements. The various elements shown in the figures that follow may be optional depending on a given embodiment without departing from the principles provided in this disclosure.

FIG. 10 shows an example interface for the job manager, according to one embodiment.

FIG. 11 shows an example interface for sharing a job with another consulting partner/recipient, according to one embodiment.

FIG. 12 shows an example interface for showing who is sharing a job, according to one embodiment.

FIG. 13 shows an example interface for displaying a third party agreement (TPA) record, according to one embodiment.

FIG. 14 shows an example interface for adding consulting partners or recipient to a previously shared job, according to one embodiment.

FIG. 15 shows an example interface of a consulting partner or recipient receiving a request to access data of a completed job, according to one embodiment.

FIG. 17 shows an example interface for allowing a user of share data to change specific properties of the shared data, according to one embodiment.

FIG. 18 shows an example interface for allowing a user of shared data to change target location and information of the shared data for analysis, according to one embodiment.

FIGS. 21A-21B show flowcharts illustrating a method for managing and accessing data using one or more data cloud servers, according to one embodiment.

DETAILED DESCRIPTION

The figures and descriptions provided herein may have been simplified to illustrate aspects that are relevant for a clear understanding of the herein described devices, systems, and methods, while eliminating, for the purpose of clarity, other aspects that may be found in typical similar devices, systems, and methods. Those of ordinary skill may recognize that other elements and/or operations may be desirable and/or necessary to implement the devices, systems, and methods described herein. But because such elements and operations are well known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

The terminology used herein is for the purpose of describing particular example embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc., may be used herein to describe various elements, components, regions, layers and/or sections, these elements, components, regions, layers and/or sections should not be limited by these terms. These terms may be only used to distinguish one element, component, region, layer or section from another element, component, region, layer or section. That is, terms such as "first," "second," and other numerical terms, when used herein, do not imply a sequence or order unless clearly indicated by the context.

System Environment

Figure 1:
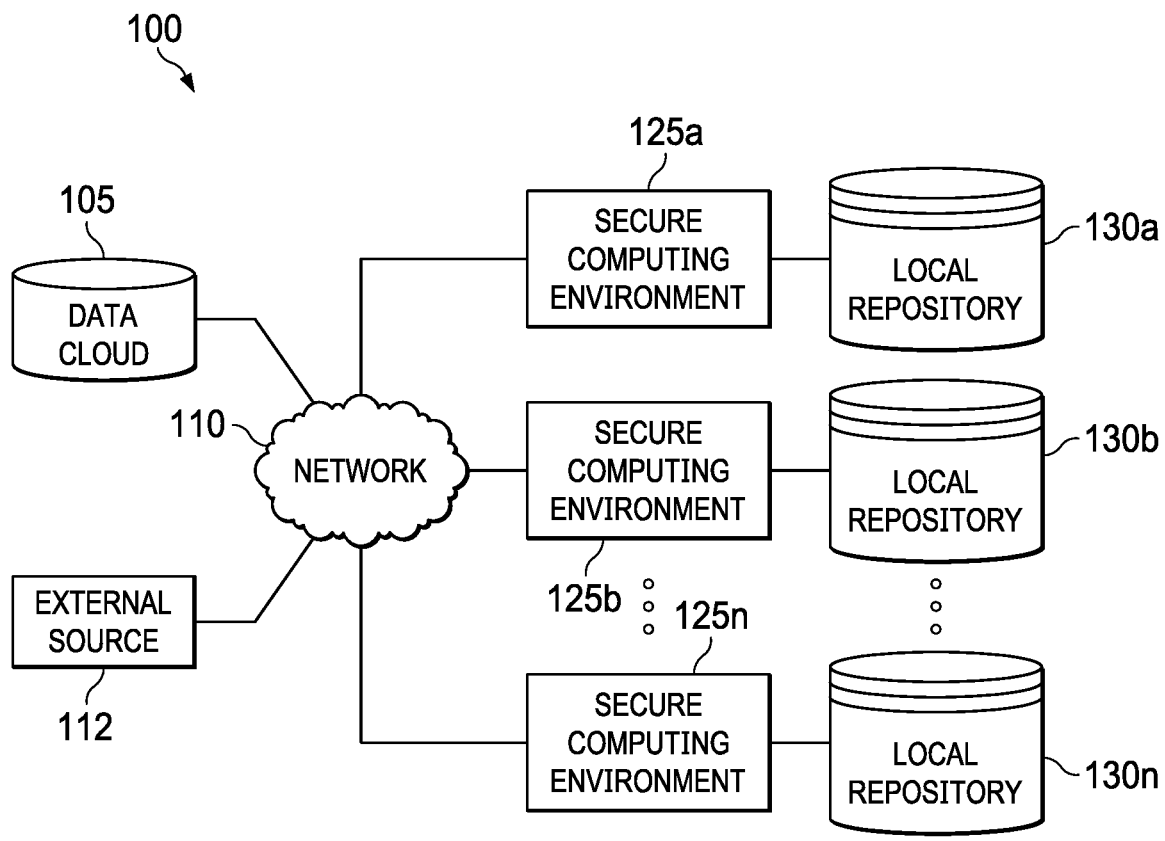
FIG. 1 is a high-level network system for accessing, managing, and sharing structured data, according to one embodiment.

Illustrated in FIG. 1 is a high level network system 100 for generating interfaces that access, maintain, analyze, and display structured data. In the depicted implementation, the system 100 may include a data cloud server 105 communicatively coupled to a plurality of secure computing environments 125 external sources 112 via the network 110. The secure computing environments 125 may in turn be communicatively coupled to a local repository 130. While a single data cloud server 105 is illustrated, the disclosed principles and techniques could be expanded to include multiple data cloud servers 105.

The data cloud server 105, according to some embodiments, is configured to store a plurality of structured data in a secure environment requiring authentication before access is granted to the structured data. According to one implementation, the structured data includes hierarchical data having varying and connected categories/levels that describe a plurality of aspects of the structured data. In some cases, the structured data in the data cloud server 105 is sourced or obtained from third-party scientific sources, and/or from third-party regulatory agencies, and/or from academic sources, and/or from industrial sources, etc.

In addition, the data cloud server 105 may be configured to manage or otherwise maintain the integrity and/or version updates of the structured data so that a user (e.g., a user of the secure computing environment) does not have to deal with such data maintenance processes as the structured data changes and/or grows. In one embodiment, the data cloud server 105 provides the most current version of the structured data to a user of the system. In other embodiments, the data cloud server 105 can also provide historical versions of the structured data when necessary or needed. Furthermore, the data cloud server 105 may include mechanisms that execute operations of data decompression operations, data decryption operations, and data decoding operations associated with the structured data so that the user is effectively isolated from such operations.

Moreover, the data cloud server 105 allows for easy associating, tagging, or coding of information for retrieval purposes. In some cases, the tagging or coding is automatically executed by the data cloud server 105. In addition, the data cloud server 105 allows a user (e.g., user of the secure computing environment 125) to transition from accessing structured data from the local repository 130 to the data cloud server 105.

The data cloud server 105 may be implemented within a computing device such as a mainframe server, a content server, a communication server, a laptop computer, a desktop computer, a handheld computing device, a virtual machine, a cloud-based computing solution and/or service, and/or the like. The data cloud server 105 may include a plurality of computing devices configured to communicate with one another and/or implement the techniques described herein. In some instances, the data cloud server 105 may include various elements of a computing environment as described with reference to FIGS. 2A and/or 2B. For example, the data cloud server 105 may include a processing system 202, a memory 204, an input/output (I/O) system 206, and a communication system 208. A user (e.g., a database administrator) may operate/maintain the data cloud server 105 either locally or remotely as the case may require.

The data cloud server 105 may be configured to have storage logic that is executable to store structured data that is shared across multiple secure computing environments 125. According to one implementation, the data cloud server 105 may include a plurality of non-volatile/non-transitory storage media such as solid state storage media, hard disk storage media, virtual storage media, cloud-based storage drives, storage servers, and/or the like. The plurality of storage media may be configured to store data from a plurality of sources. For example, the data cloud server 105 may include storage logic that is executable to store structured data derived from, for example, medical data, research data, education data, government data, etc. According to some implementations, the storage logic of the data cloud server 105 may be configured to automatically monitor and/or update relevant structured data obtained from a third-party source. For example, the storage logic of the data cloud server 105 may periodically monitor updates associated with structured data (e.g., dictionary of medical terms for research and regulatory purposes) from third-party organizations/sources and automatically update different versions of the structured data within one or more storage media of the data cloud server 105. In one embodiment, the storage logic of the data cloud server 105 manipulates or otherwise formats the structured data such that user interfaces generated by a secure computing environment 125 can seamlessly access/retrieve and present the structured data to a user. In addition, structured data from the data cloud server 105 may be accessed on a regulated basis via credential access, for example. This regulated basis may be determined, in part, by licenses, privileges, and other levels of authorization dictated by a user's credentials.

The external source 112 may operate similarly like the data cloud server 105 including having all the technical features of the data cloud server 105 described herein. The difference between the external source 112 and the data cloud server 105 is the external source 112 operates in providing information to the data cloud server 105 when requested. While a single external source 112 is illustrated, the disclosed principles and techniques could be expanded to include multiple external sources 112.

The local repository 130 may include storage logic for storing a local copy of structured data from the data cloud server 105. The local repository 130 may also be configured to store data other than the structured data. For example, the local repository 130 may store data from third-party sources and other data generated by the secure computing environment 125. The local repository may include a plurality of non-volatile/non-transitory storage media such as solid state storage media, hard disk storage media, virtual storage media, cloud-based storage drives, storage servers, and/or the like. According to some embodiments, the local repository 130 may include logic that updates structured data stored within its storage devices based on updates to structured data stored within the data cloud server 105. In some cases, snapshots of structured data may be accessed using the secure computing environment 125 so that updates associated with the snapshots may be effected on the local repository 130.

As previously discussed, the network 110 facilitates communication between the data cloud server 105, the external source 112, and the secure computing environment 125. The network 110 may also allow different secure computing environments 125 to communicate with each other. According to one embodiment, the network 110 may include a plurality of networks. For instance, the network 110 may include any wired/wireless communication network that facilitates communication between the components of the network system 100. The network 110, in some instances, may include an Ethernet network, a cellular network, a computer network, the Internet, a wireless fidelity (Wi-Fi) network, a light fidelity (Li-Fi) network, a Bluetooth network, a radio frequency identification (RFID) network, a near-field communication (NFC) network, a fiber optics network, a laser-based network, and/or the like.

The secure computing environment 125 is configured to generate one or more user interfaces for accessing, analyzing, and displaying the structured data. According to some implementations, the secure computing environment 125 includes functionalities and/or enhanced security features that allow a user to securely access and/or securely manage structured data. As shown more clearly in the exemplary functional and system diagrams of FIGS. 2A and 2B, the secure computing environment 125 includes a processing system 202, a memory 204, and I/O system 206, and a communication system 208. The processing system 202, the memory 204, the I/O system 206, and the communication system 208 may include one or more subsystems that perform one or more of the operations described herein. Additionally, each system of the secure computing environment 125 may be operatively and/or otherwise communicatively coupled with each other so as to facilitate one or more operations described herein. The secure computing environment 125 may include general hardware, specifically-purposed hardware, and/or a combination thereof.

Figure 2A:
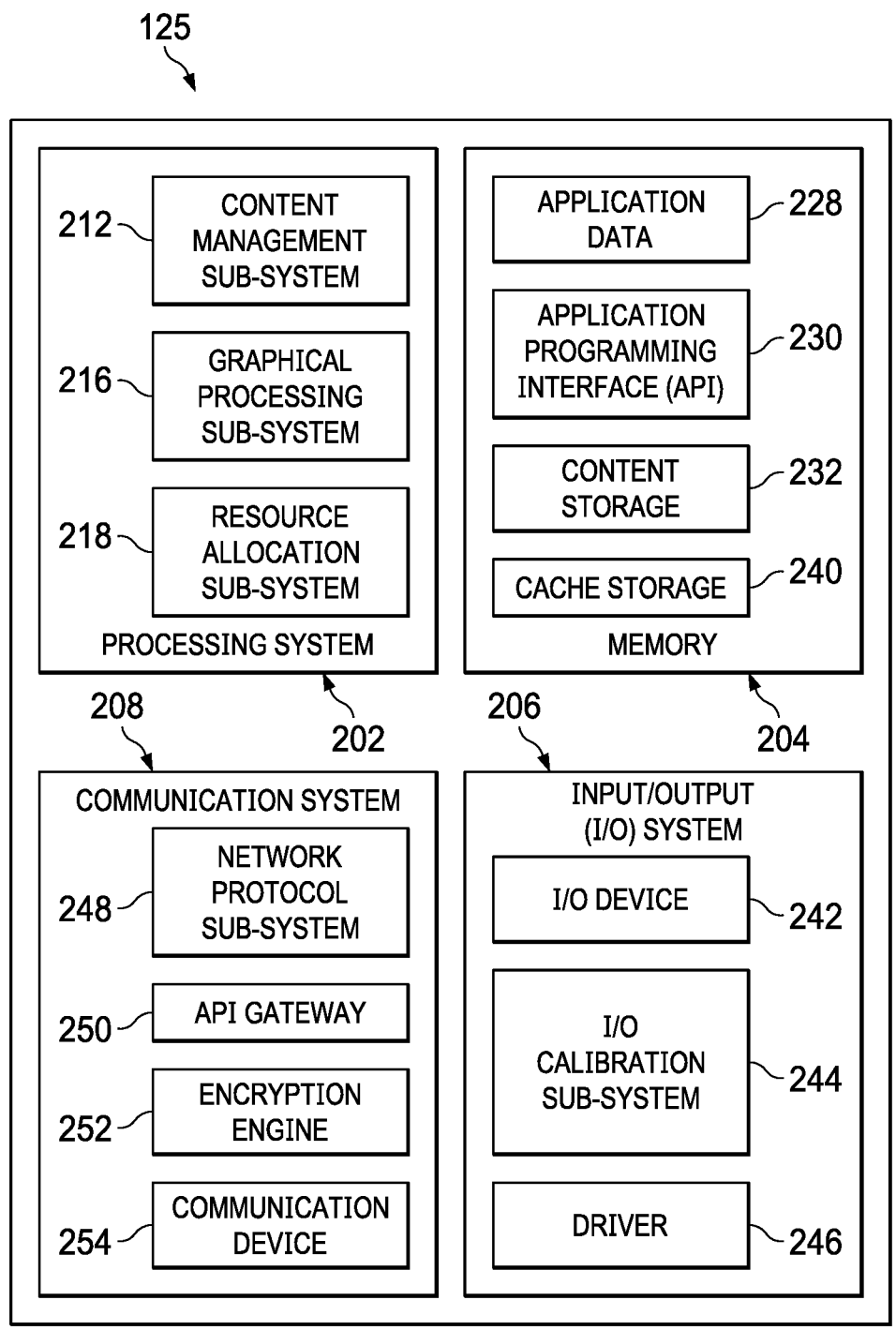
FIG. 2A is a functional block diagram of a computing environment for accessing and visualizing structured data, according to one embodiment.
Figure 2B:
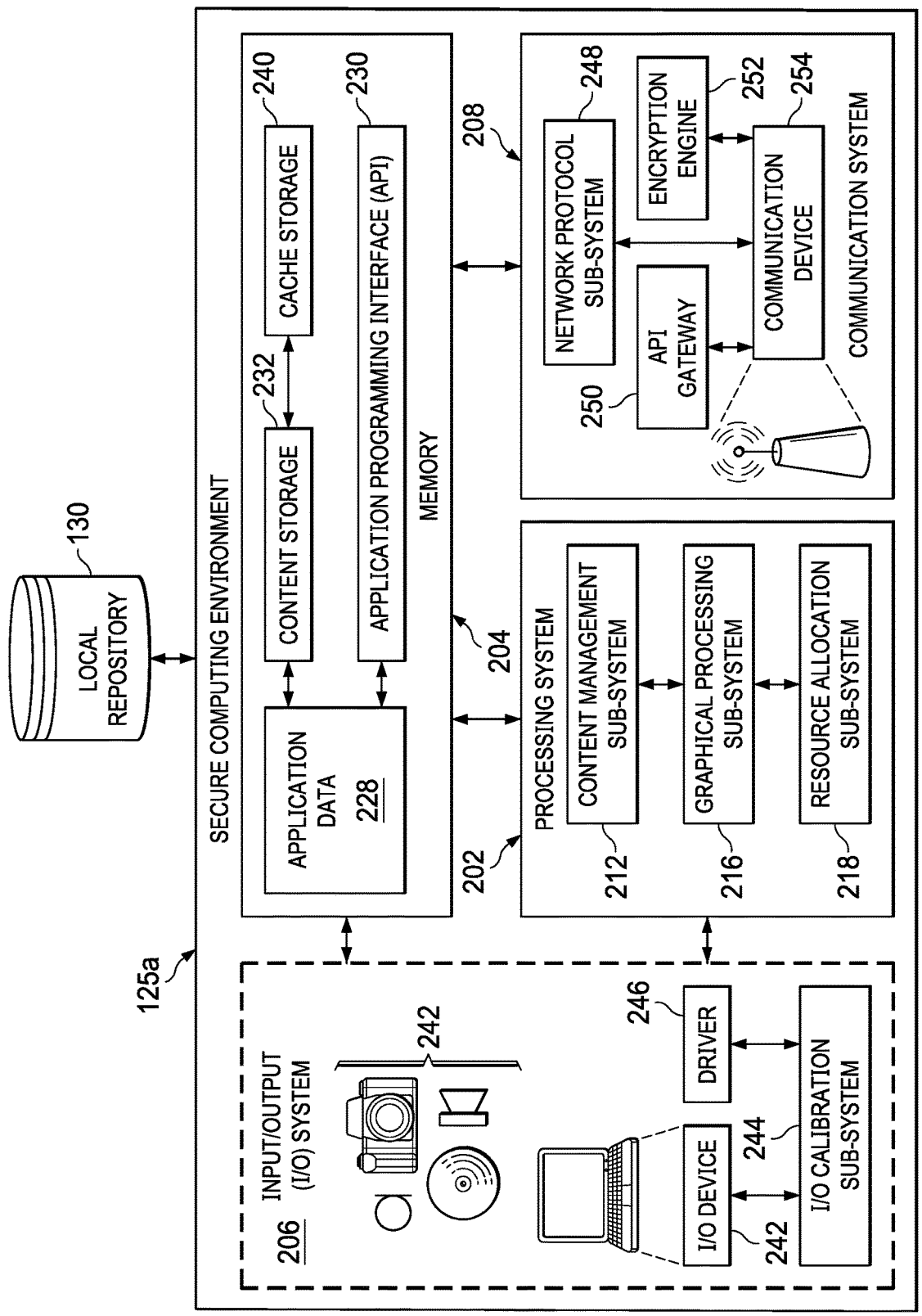
FIG. 2B is a detailed system diagram of FIG. 2A, according to one embodiment.

The processing system 202 may control the memory 204, the I/O system 206, and the communication system 208, as well as any included subsystems, elements, components, devices, and/or functions performed by the memory 204, I/O system 206, and the communication system 208. Additionally, any actions described in this disclosure as being performed by a processor or one or more processors of a computing device or one or more computing device processors and/or one or more computing system processors may be executed by the processing system 202 of FIGS. 2A and 2B. Further, while one processing system 202 is shown in FIGS. 2A and 2B, multiple processing systems may be present and/or otherwise included in the secure computing environment 125 or elsewhere in the overall network system 100 of FIG. 1. Thus, while instructions may be described as being executed by the processing system 202 (and/or various subsystems of the processing system 202), the instructions may be executed simultaneously, serially, and/or otherwise by one or multiple processing systems 202 on one or more computing devices.

According to one embodiment, the processing system 202 may be implemented as one or more computer processor chips and/or graphical processing unit (GPU) chips and may include a hardware device capable of executing computer instructions. The processing system 202 may execute instructions, codes, computer programs, and/or scripts. The instructions, codes, computer programs, and/or scripts may be received from the I/O system 206, the communication system 208, and/or stored in the memory 204, and/or received from the other subsystems of the secure computing environment 125 and/or received from other computing environments.

In some embodiments, the processing system 202 may include subsystems such as a content management subsystem 212, a graphical processing subsystem 216, and a resource allocation subsystem 218. Each of the aforementioned subsystems of the processing system 202 may be communicatively or operably coupled to each other.

The content management sub-system 212 may facilitate generation, modification, analysis, transmission, and/or presentation of content. Content may be file content, media content, structured data content, user interfaces, or any combination thereof. In some instances, content on which the content management system 212 operates includes structured data from the data cloud server 105, structured data from the local repository 130, user interface data, device information, images, text, themes, audio files, video files, documents, and/or the like. Additionally, the content management subsystem 212 may control the audio-visual environment and/or appearance of application data during execution of various processes. In some embodiments, the content management subsystem 212 may interface with a third-party content server and/or third-party memory locations for execution of its operations.

The graphical processing subsystem 216 may facilitate generation, modification, analysis, processing, transmission, and/or presentation of the content described above, as well as any data described herein. In some embodiments, the graphical processing subsystem 216 may be used to render content for presentation on a computing device (e.g., via a graphical user interface of the computing device). The graphical processing subsystem 216 may also include multiple graphical processing subsystems and therefore may be configured to perform and/or execute multiple processes in parallel. In some implementations, the graphical processing subsystem 216 may be used in conjunction with components of the memory 204, the I/O system 206, the communication system 208, and/or a combination thereof.

The resource allocation subsystem 218 may facilitate the determination, monitoring, analysis, and/or allocation of computing resources throughout the secure computing environment 125 and/or other computing environments. Computing resources of the secure computing environment 125 may be used by the processing system 202, the memory 204, the I/O system 206, and/or the communication system 208. These resources may include processing power, data storage space, network bandwidth, and/or the like. Accordingly, the resource allocation subsystem 218 may include sensors and/or other specially-purposed hardware for monitoring performance of each system and/or subsystem of the secure computing environment 125, as well as hardware for responding to the computing-resource needs of each system and/or subsystem. In some embodiments, the resource allocation subsystem 218 may use computing resources of a second secure computing environment separate and distinct from the secure computing environment 125 to facilitate a desired operation.

The memory 204 may be used for storing, recalling, receiving, transmitting, and/or accessing various files and/or data (e.g., structured data) during the operation of the secure computing environment 125. For example, the memory 204 may store, recall, and/or update structured data from the data cloud and/or the local repository as the case may be. In some embodiments, the memory 204 may store instructions and/or data that may be executed by the processing system 202. For instance, the memory 204 may store instructions that execute operations associated with one or more systems and/or one or more subsystems of the secure computing environment 125. For example, the memory 204 may store instructions for the processing system 202, the I/O system 206, the communication system 208, and for itself.

Memory 204 may include various types of data storage media such as solid state storage media, hard disk storage media, virtual storage media, and/or the like. Memory 204 may include dedicated hardware elements such as hard drives and/or servers, as well as software elements such as cloud-based storage drives. In some implementations, memory 204 may be a random access memory (RAM) device, a dynamic random access memory (DRAM) device, a static random access memory (SRAM) device, flash memory, read only memory (ROM) device, and/or various forms of secondary storage. The RAM device may be used to store volatile data and/or to store instructions that may be executed by the processing system 202. For example, the instructions stored may be a command, a current operating state of secure computing environment 125, an intended operating state of secure computing environment 125, and/or the like. As a further example, data stored in the memory 204 may include instructions related to various methods and/or functionalities described herein. The ROM device may be a non-volatile memory device that may have a smaller memory capacity than the memory capacity of a secondary storage of the secure computing environment. The ROM device may be used to store instructions and/or data that may be read during execution of computer instructions. In some embodiments, access to both the RAM device and ROM device may be faster to access than access to the secondary storage of the secure computing environment 125. Secondary storage may comprise one or more disk drives and/or tape drives which may be used for non-volatile/non-transitory storage of data or as an over-flow data storage device of the secure computing environment 125 if the RAM device is not large enough to hold all working data. Secondary storage may be used to store programs that may be loaded into the RAM device when such programs are selected for execution.

Turning back to FIG. 2A, the memory 204 may include subsystems such as application data 228, application programming interface 230, content storage 232, and cache storage 240. Application data 228 may facilitate deployment, storage, access, execution, and/or utilization of an application utilized by the secure computing environment 125 and/or any other computing environments described herein. As such, application data 228 may store any information and/or data associated with an application. Application data 228 may further store various pieces of information and/or data associated with the operation of an application and/or with the secure computing environment 125 as a whole, such as a status of computing resources (e.g., processing power, memory availability, resource utilization, and/or the like), runtime information, user interfaces, systems to direct execution of operations described herein to, user permissions, security credentials, and/or the like.

The application programming interface (API) 230 may facilitate deployment, storage, access, execution, and/or utilization of information associated with APIs of secure computing environment 125 and/or any other computing environment described herein. For example, secure computing environment 125 may include one or more APIs for various devices, applications, systems, subsystems, elements, and/or other computing environments to allow communication between one or more applications associated with the secure computing environment 125. Accordingly, API 230 may include API databases containing information that may be accessed and/or used by applications, systems, subsystems, elements, and/or operating systems of other devices and/or computing environments in communication with the secure computing environment 125. In some cases, the API 230 may enable the data cloud server 105 and the secure computing environment 125 to communicate with each other.

The content storage 232 may facilitate deployment, storage, access, and/or utilization of information associated with structured data as further discussed below. In one embodiment, content storage 232 may communicate with a content management system 212 to receive and/or transmit content (e.g., structured data, media content, etc.).

The I/O system 206 may include hardware and/or software elements for the secure computing environment 125 to receive, and/or transmit, and/or present information useful for generating one or more interfaces for retrieving and displaying structured data according to some embodiments of this disclosure. For example, elements of the I/O system 206 may be used to receive input from a user of the secure computing environment 125. As described herein, I/O system 206 may include subsystems such as I/O device 242, I/O calibration subsystem 244, and/or driver 246.

The I/O device 242 may facilitate the receipt, transmission, processing, presentation, display, input, and/or output of information as a result of executed processes described herein. In some embodiments, the I/O device 242 may include a plurality of I/O devices. In some embodiments, I/O device 242 may include a variety of elements that enable a user to interface with secure computing environment 125. For example, I/O device 242 may include a keyboard, a touchscreen, a button, a sensor, a biometric scanner, a laser, a microphone, a camera, and/or another element for receiving and/or collecting input from a user. Additionally and/or alternatively, I/O device 242 may include a display, a screen, a sensor, a vibration mechanism, a light emitting diode (LED), a speaker, a radio frequency identification (RFID) scanner, and/or another element for presenting and/or otherwise outputting data to a user. In some embodiments, the I/O device 242 may communicate with one or more elements of processing system 202 and/or memory 204 to execute operations associated with generating user interfaces for retrieving and visualizing structured data.

The I/O calibration system 244 may facilitate the calibration of the I/O device 242. For example, I/O calibration system 244 may detect and/or determine one or more settings of I/O device 242, and then adjust and/or modify settings so that the I/O device 242 may operate more efficiently. In some embodiments, I/O calibration system 244 may use a driver 246 (or multiple drivers) to calibrate I/O device 242 as needed. For example, driver 246 may include software that is to be installed by I/O calibration system 244 so that an element of secure computing environment 125 (or an element of another computing environment) may recognize and/or integrate with I/O device 242.

The communication system 208 may facilitate establishment, maintenance, monitoring, and/or termination of communications between the secure computing environment 125 and other computing environments, third-party server systems, and/or the like. Communication system 208 may also facilitate internal communications between various elements (e.g., systems and/or subsystems) of secure computing environment 125. In some embodiments, communication system 208 may include a network protocol subsystem 248, an API gateway 250, an encryption engine 252, and/or a communication device 254. These systems and/or subsystems of the communication system 208 may be implemented as hardware, software, or a combination thereof.

The network protocol subsystem 248 may facilitate establishment, maintenance, and/or termination of a communication connection for the secure computing environment 125 via a network (e.g., network 110). For example, network protocol subsystem 248 may detect and/or define a communication protocol required by a particular network and/or network type. Communication protocols utilized by network protocol subsystem 248 may include Wi-Fi protocols, Li-Fi protocols, cellular data network protocols, Bluetooth® protocols, internet protocols, WiMAX protocols, Ethernet protocols, power line communication (PLC) protocols, and/or the like. In some embodiments, facilitation of communication for the secure computing environment 125 may include transforming and/or translating data from a first communication protocol to a second communication protocol. In some embodiments, network protocol subsystem 248 may determine and/or monitor an amount of data traffic to determine which network protocol is to be used for establishing a secure communication connection, transmitting data, and/or performing retrieval and subsequent visualization of structured data.

The application programming interface (API) gateway 250 may allow other devices and/or computing environments and/or applications external to the secure computing environment 125 to access the API 230 of the memory 204. For example, a computing system may access the API 230 of the secure computing environment 125 via the API gateway 250. In some embodiments, API gateway 250 may be required to validate user credentials associated with a user of a computing device (e.g., a device external to the secure computing environment 125) prior to providing access to the API 230 to the user. API gateway 250 may include instructions for the secure computing environment 125 and thereby communicate with external devices and/or between components of the secure computing environment 125.

The encryption engine 252 may facilitate translation, encryption, encoding, decryption, and/or decoding of information received, transmitted, and/or stored by the secure computing environment 125. Using encryption engine 252, each transmission of data may be encrypted, encoded, and/or translated for security reasons, and any received data may be encrypted, encoded, and/or translated prior to its processing and/or storage. In some embodiments, encryption engine 252 may generate an encryption key, an encoding key, a translation key, and/or the like, which may be transmitted along with any data content.

The communication device 254 may include a variety of hardware and/or software specifically purposed to facilitate communication for secure computing environment 125 with external systems and/or devices. In some embodiments, communication device 254 may include one or more radio transceivers, chips, analog front end (AFE) units, antennas, processing units, memory, other logic, and/or other components to implement communication protocols (wired or wireless) and related functionality for facilitating communication for system 125. Additionally and/or alternatively, communication device 254 may include a modem, a modem bank, an Ethernet device such as a router or switch, a universal serial bus (USB) interface device, a serial interface, a token ring device, a fiber distributed data interface (FDDI) device, a wireless local area network (WLAN) device and/or device component, a radio transceiver device such as code division multiple access (CDMA) device, a global system for mobile communications (GSM) radio transceiver device, a universal mobile telecommunications system (UMTS) radio transceiver device, a long term evolution (LTE) radio transceiver device, a worldwide interoperability for microwave access (WiMAX) device, and/or another device used for communication purposes.

User Interfaces

In performing the operations shown in FIGS. 3-20, the example interfaces described herein may communicate with data cloud server 105 to access information either from the data cloud server 105 or the external source 112. The example interfaces described herein may be implemented on the secure computing environment 125 or alternatively on even a separate server/computer system coupled to network 110. Moreover, the example user interfaces described herein may utilize the communication resources of the secure computing environment 125 described herein to communicate with data cloud server 105. In addition, example user interfaces described in FIGS. 3-20 may utilize the communication resources of the separate server/computer system to communicate with data cloud server 105.

Figure 3:
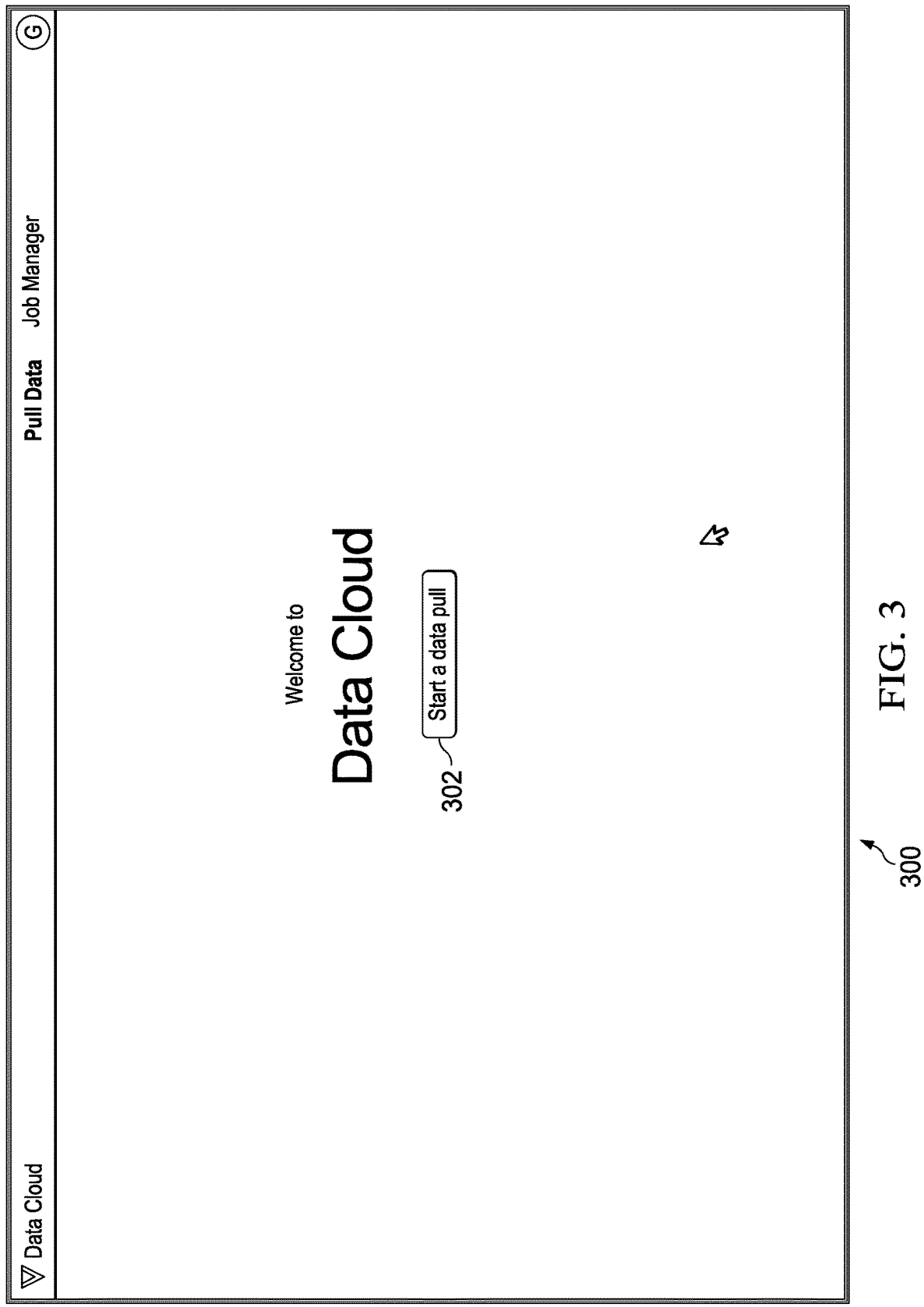
FIG. 3 shows an example interface used to initiate a data pull process to access the resources of a data cloud server, according to one embodiment.

FIG. 3 illustrates an example interface 300 used to access the resources of the data cloud server 105, according to one embodiment. The example interface 300 may be an introductory interface a user utilizes to access information using data cloud server 105. Also, the example interface 300 may include a data pull button 302 to initiate a data pull process once the user clicks button 302. The data pull process may involve retrieving data from one or more external sources 112 for analysis.

Figure 4:
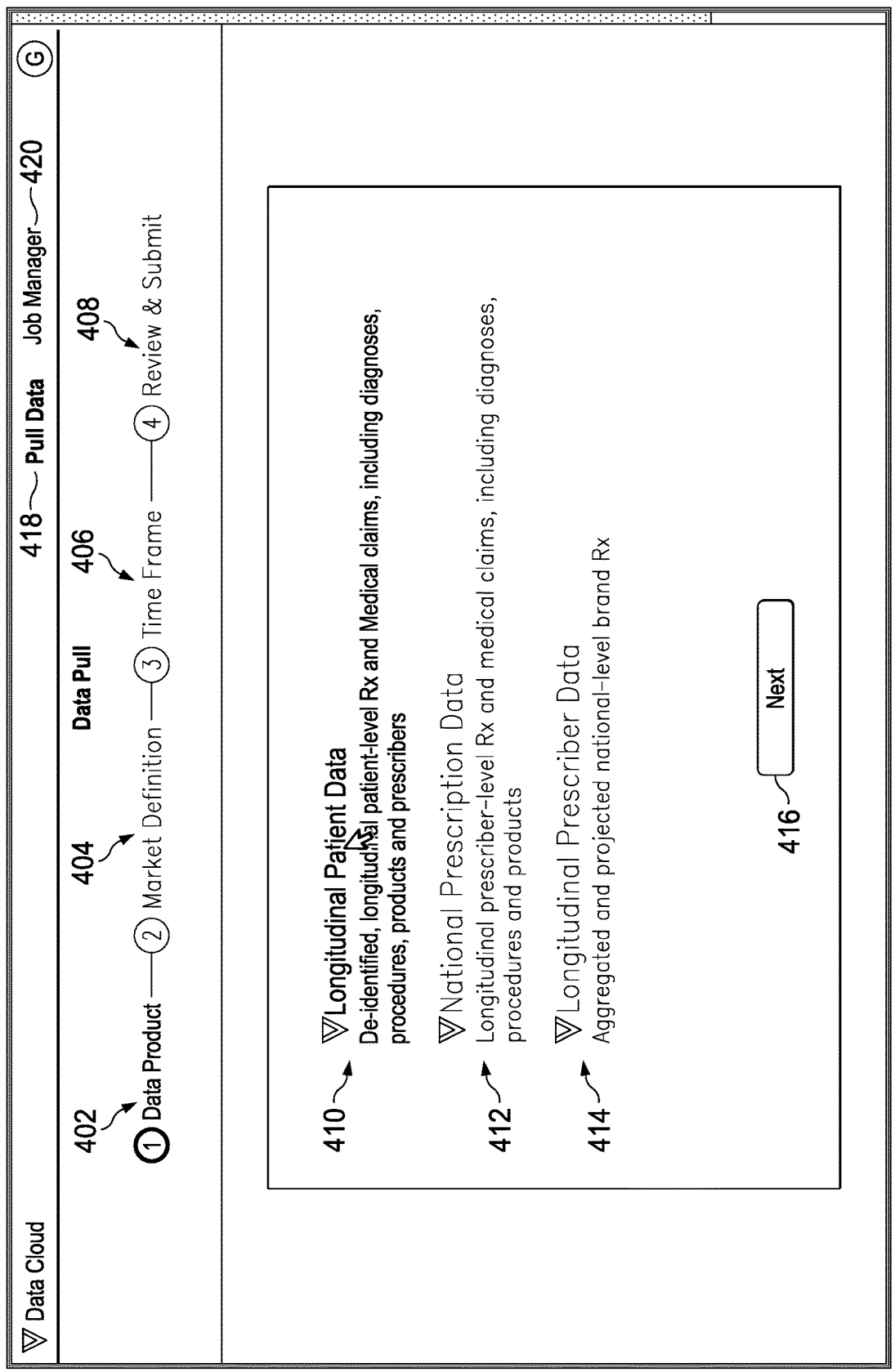
FIG. 4 shows an example interface for configuring the product used for the data pull, according to one embodiment.

FIG. 4 shows an example interface 400 for configuring the data product used for the data pull, according to one embodiment. The example interface 400 may include a number of processing stages 402-408 used in the exemplary data pull process. Currently, example interface 400 may indicate it is under the Data Product processing stage 402 involving identifying which particular types of data the user wants to retrieve. The other status processing stages may include market definition 404, time frame stage 406, and review and submit stage 408. The other processing stages will be further discussed below in FIGS. 5-10.

The example interface 400 may include the following data products: (1) Longitudinal Patient Data 410; (4) National Prescription Data 412; and (3) Longitudinal Prescriber Data 414. The Longitudinal Patient Data 410 may include de-identified, longitudinal patient level data. In some embodiments, the longitudinal patient level data may include prescription and medical claims, including diagnoses, procedures, and prescribers. The National Prescription Data 412 may include longitudinal prescriber level prescription and medical claims. The Longitudinal Prescriber Data 414 may involve aggregated and protected national level brand prescription information. The example interface 400 may allow a user to select one or more data products for the data pull process. After one or more of the data products have been selected, the user may press or click a next button 416 to continue processing. In this case, the data product selected for processing was the Longitudinal Patient Data 410.

In some implementations, additional data products beside those shown in example interface 400 may be provided.

Figure 5:
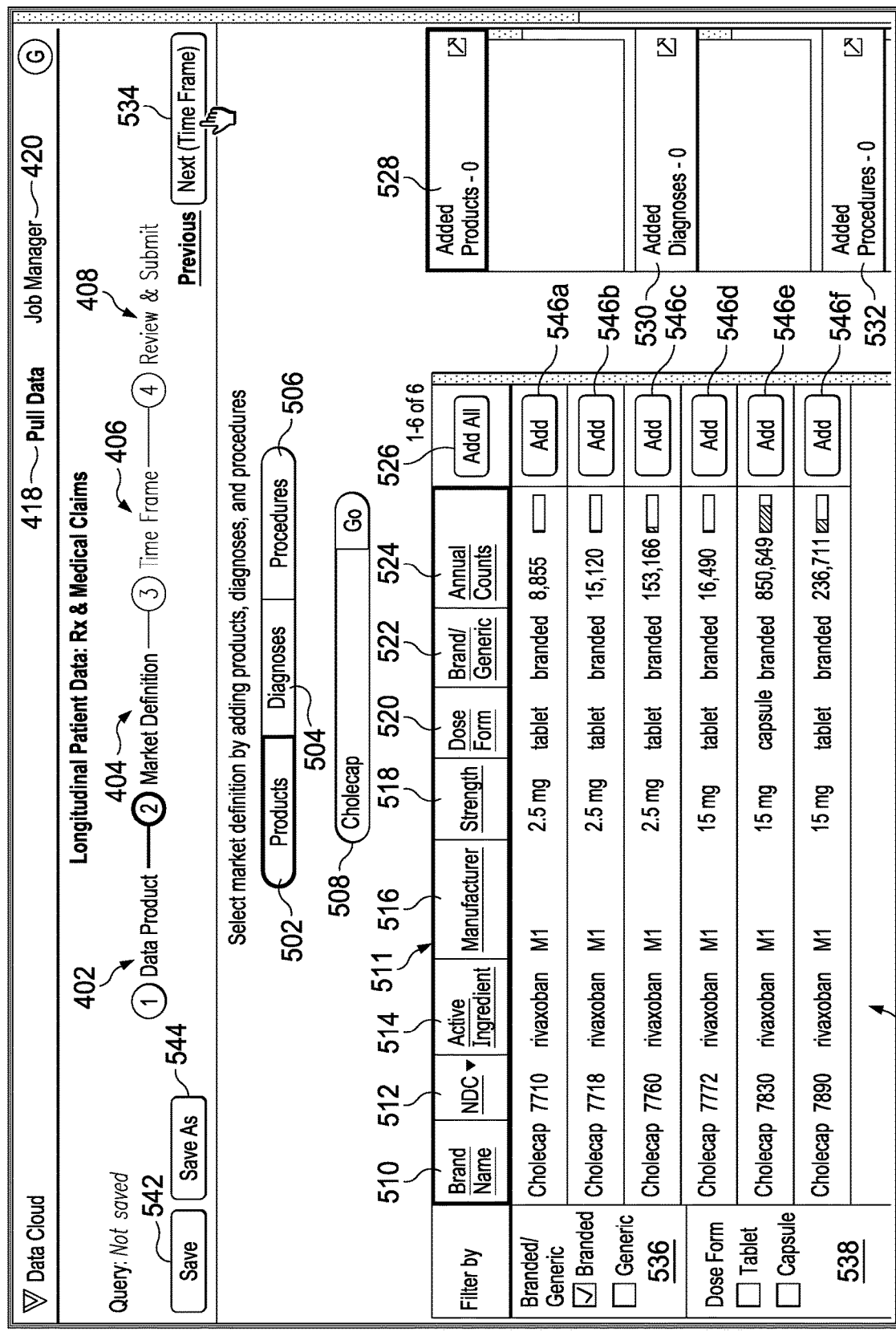
FIG. 5 shows an example interface for defining the market definition of the data to be uploaded for processing, according to one embodiment.

FIG. 5 shows an example interface for defining the market definition of the data to be uploaded for processing, according to one embodiment. After clicking the button 416, the example interface 500 appears to be in the market definition processing stage 404. The market definition processing stage 404 may validate and confirm the specific market data used in the data pull process. To select the appropriate market definition, one may select the products, diagnosis, and procedures used. The example interface 500 may provide a product button 502, a diagnosis button 504, and a procedure button 506 to input the parameters for the market definition. In this case, product button 502 may be active and the user inputs in search text box 508 a fictitious product Cholecap and enters this information via button 509 to extract product search results.

The example interface 500 may include a table listing defining the content of the search results 540. The table listing 511 may include the following fields: Brand Name 510, NDC 512, Active ingredients 514, Manufacturer 516, strength 518, Dose Form 520, Brand/Generic 522, and Annual count 524. Moreover, the table listing 511 may include filter windows 536 and 538. Filter window 536 narrows the search results 540 by allowing a user to select the term "branded" or "generic" associated with the Brand/Generic field 522. While filter window 538 narrows the search results 540 by allowing a user to select the term "tablet" or "capsule" associated with the Dose Form field 520.

Also, the table listing 511 may include an Add All button 526, which adds all the search results 540 to an Added Products selection window 528. The Added Products selection window 528 may include all the relevant products to be considered in the data pull process. Each of the search results 540 may include an Add button 546a . . . 546f. In this case, the user may select a specific product search result to be added to the Added Products selection window 528. Also, example interface 500 may include an Added Diagnosis selection window 530 and an Added Procedure selection window 532. The Added Diagnosis selection window 530 may include all the relevant diagnosis to be considered in the data pull process. The Added Procedure selection window 532 may include all the relevant procedures to be considered in the data pull process.

Button 542 or 544 may provide the saving options for permanently storing the products selected for the data pull process.

Figure 6:
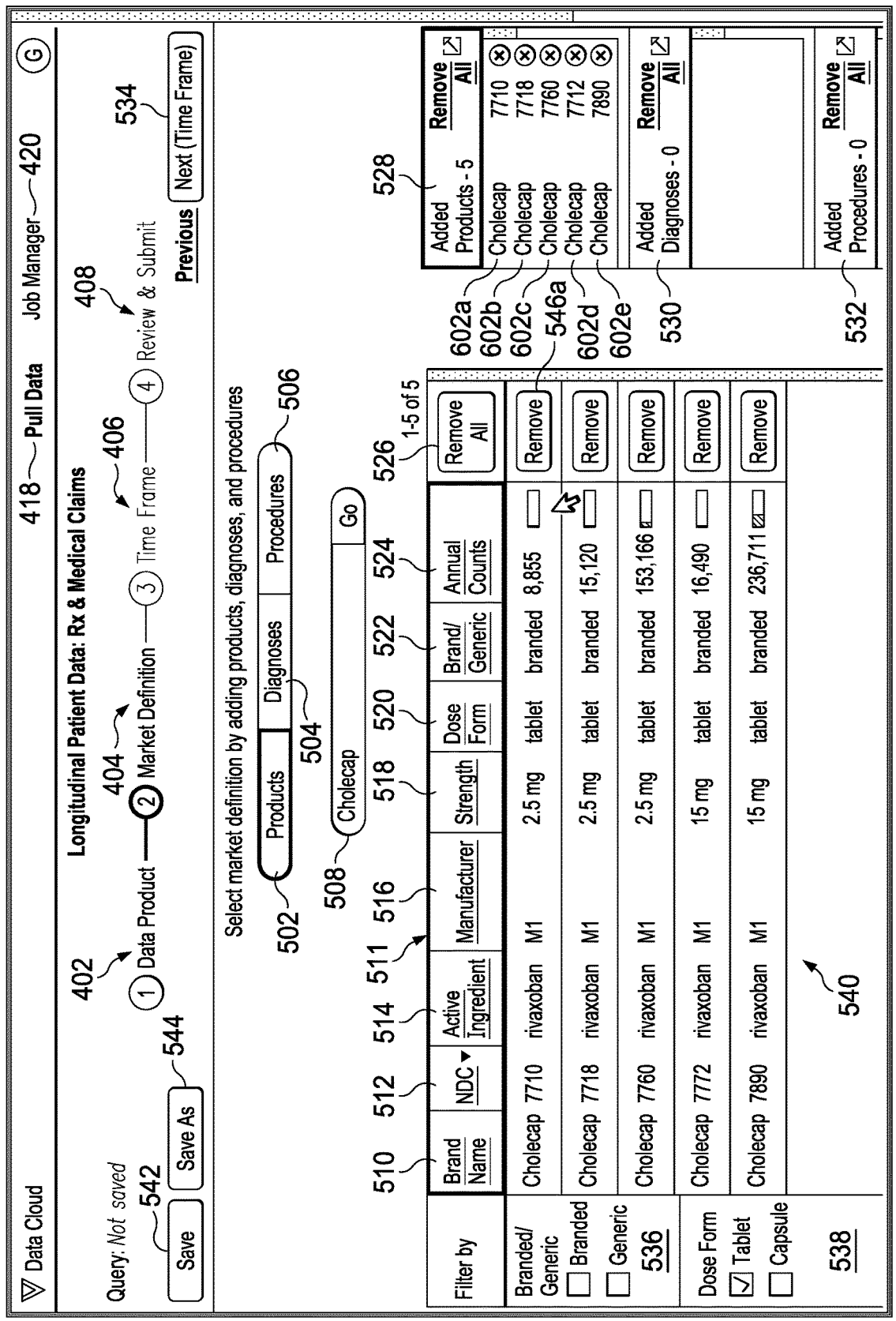
FIG. 6 shows an example interface for selecting the relevant products for the data pull process, according to one embodiment.

FIG. 6 shows an example interface 600 for selecting the relevant products for the data pull process, according to one embodiment. Note the example interface 600 is similar to the example interface 500 of FIG. 5. As shown in FIG. 6, example interface 600 is still in the market definition stage 404, but the user may now engage in adding the relevant products to be selected as part of the data pull process. In this case, the Added Products selection window 528 may include the selected products 602a . . . 602e from search result 540.

Figure 7:
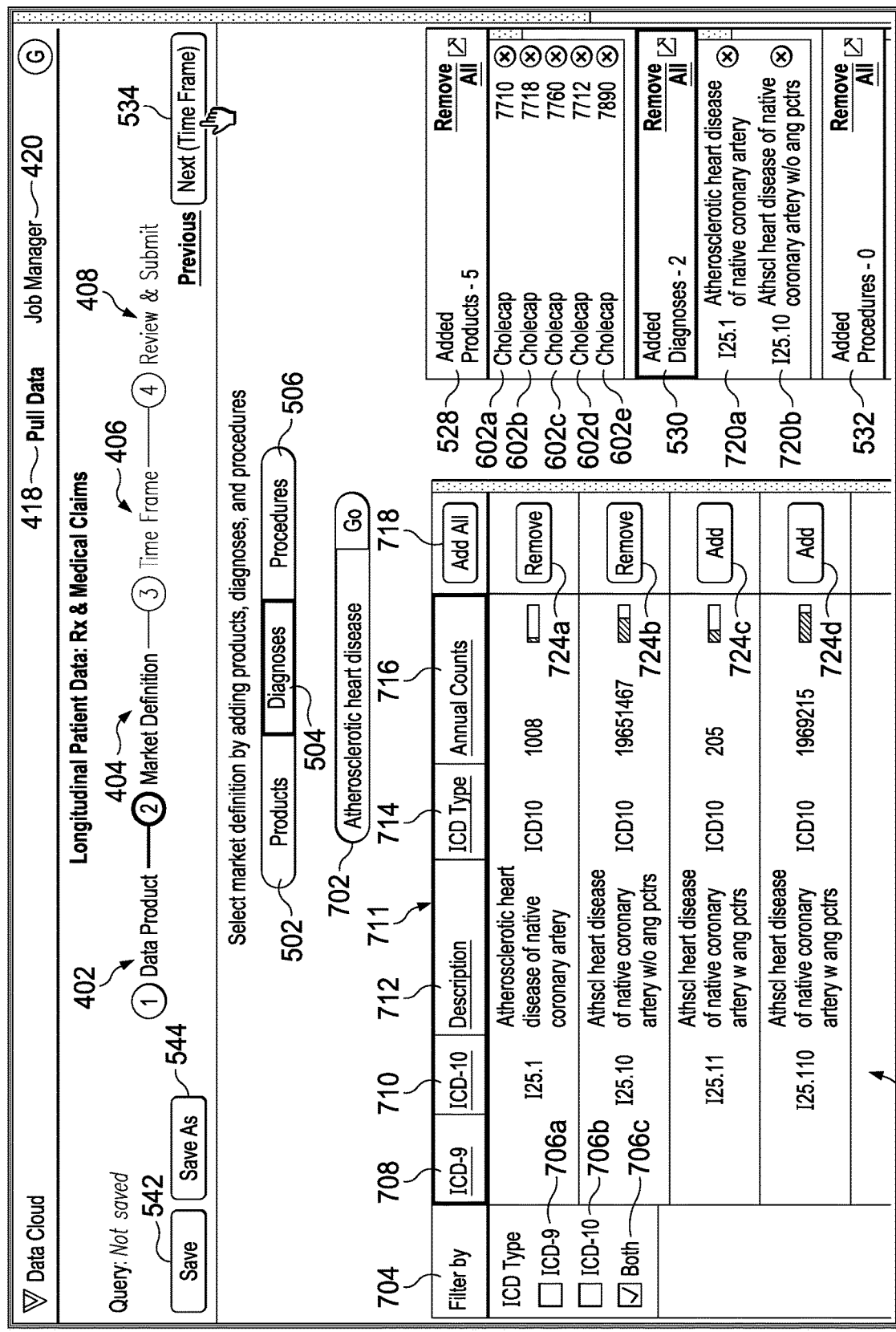
FIG. 7 shows an example interface for selecting the relevant diagnosis for the data pull process, according to one embodiment.

FIG. 7 shows an example interface 700 for selecting the relevant diagnosis for the data pull process, according to one embodiment. Note the example interface 700 is similar to the example interface 600 of FIG. 5. Example interface 700 may be in the market definition stage. The diagnosis button 504 is active and the user inputs in search text box 702, as an example, "Atherosclerotic heart disease" and enters this information via button 703 to extract diagnosis search results 722.

The example interface 700 may include a table listing 711 defining the content of the search results 722. The table listing 711 may include the following fields: ICD-9 708, ICD-10 710, Description 712, ICD-Type 714, and Annual count 716. Moreover, the table listing 711 may include filter windows 704. Filter window 704 narrows the search results 722 by allowing a user to select the search terms 706a . . . 706b associated with the ICD-Type field 714. Also, the table listing 511 may include an Add All button 718, which adds all the search results 722 to the Added Diagnosis selection window 530. Each of the search results 722 may include a Remove buttons 724a and 724b and Add buttons 724c and 724d. The user may select a specific diagnosis search result to be added to the Added Diagnosis selection window 530. In this case, the Added Diagnosis selection window 530 may include the selected diagnosis 702a . . . 720b from search result 722. Afterwards, the user select button 534 to proceed to the next stage of the data pull process.

Note the same procedures discussed for example interfaces 500 and 700 for adding information in the Added Products selection window 528 and the Added Diagnosis selection window 530 may be used to add information for the Added Product selection window 532. In particular, an example interface, similar to example interfaces 500 and 700, may be provided for selecting the relevant procedures for the data pull process. This example interface may include a text box, similar to text boxes 502 and 702, where the user enters a procedure to produce search results of a defined set. Moreover, the search results may be listed in a table listing, such as table listings 511 and 711. Also, the table listing may include number of fields defining specific properties of the search results. In addition, the example interface may include one or more buttons for adding one or more search results to the Added Product selection window 528, as in the case of example interfaces 500 and 700.

Figure 8:
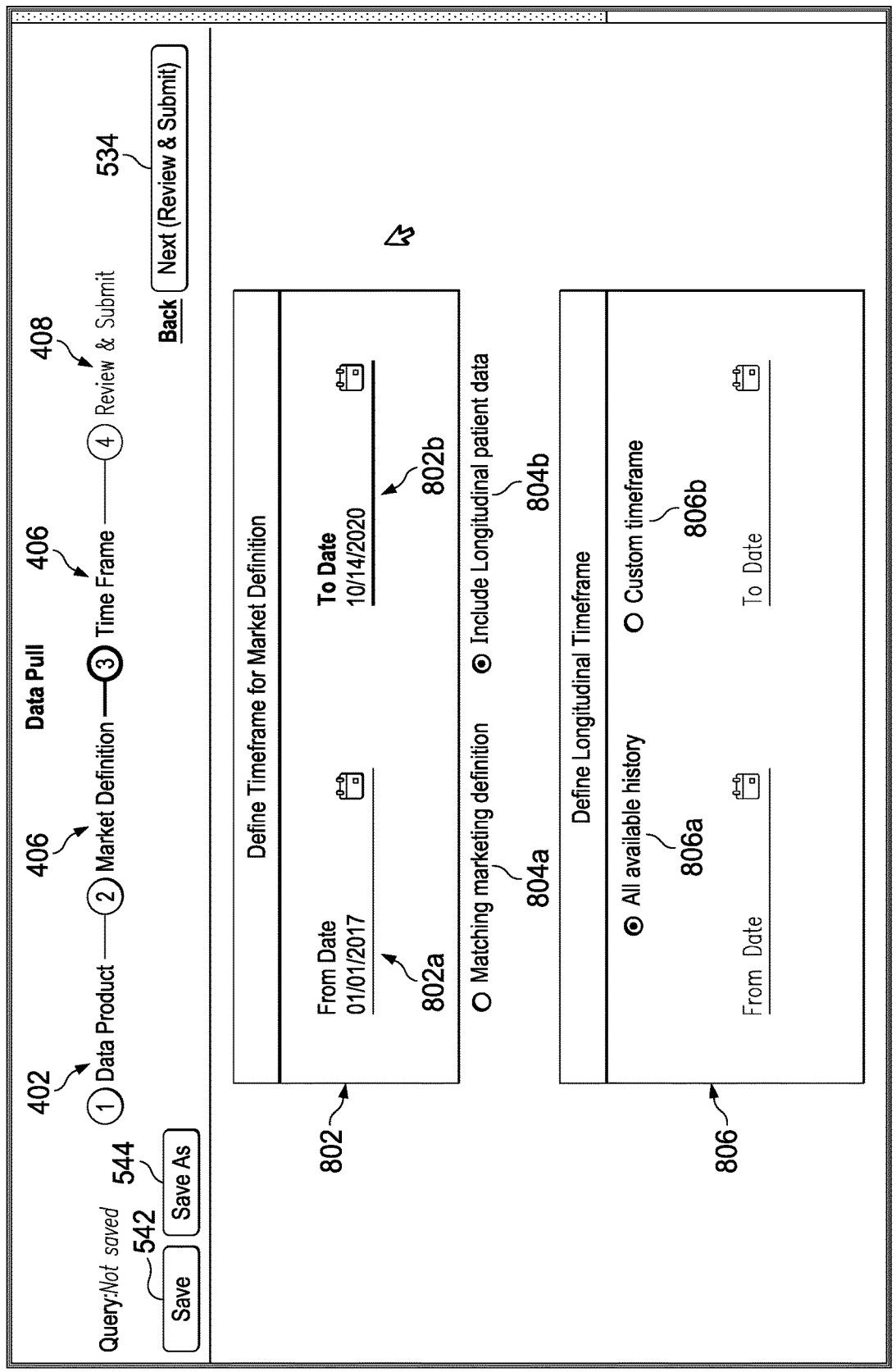
FIG. 8 shows an example interface for selecting the relevant timeframe for the data pull process, according to one embodiment.

FIG. 8 shows an example interface 800 for selecting the relevant time frame for the data pull process, according to one embodiment. Note the example interface 800 is similar to the example interface 700 of FIG. 7. As shown in FIG. 8, example interface 800 has transitioned to the time frame stage 406 where a user provides the time frame in which data is pulled. Example interface 800 may include a market definition timeframe selection box 802 having an input field 802a for entering a "From Date" and input field 802b for entering a "To Date." The user may enter the respective dates for input fields 802a and 802b. Moreover, example interface 800 may allow a user to select if the data pull process may include matching marketing definition and/or longitudinal patient data by selecting input fields 804a and/or 804b. Moreover, example interface 800 may include a longitudinal timeframe selection box 806. The longitudinal timeframe selection box 806 may allow a user to select if their longitudinal data include all available history or be defined within a custom timeframe by selecting input fields 806a and/or 806b. Afterwards, the user may select a button 534 to proceed to the next stage of the data pull process.

Figure 9:
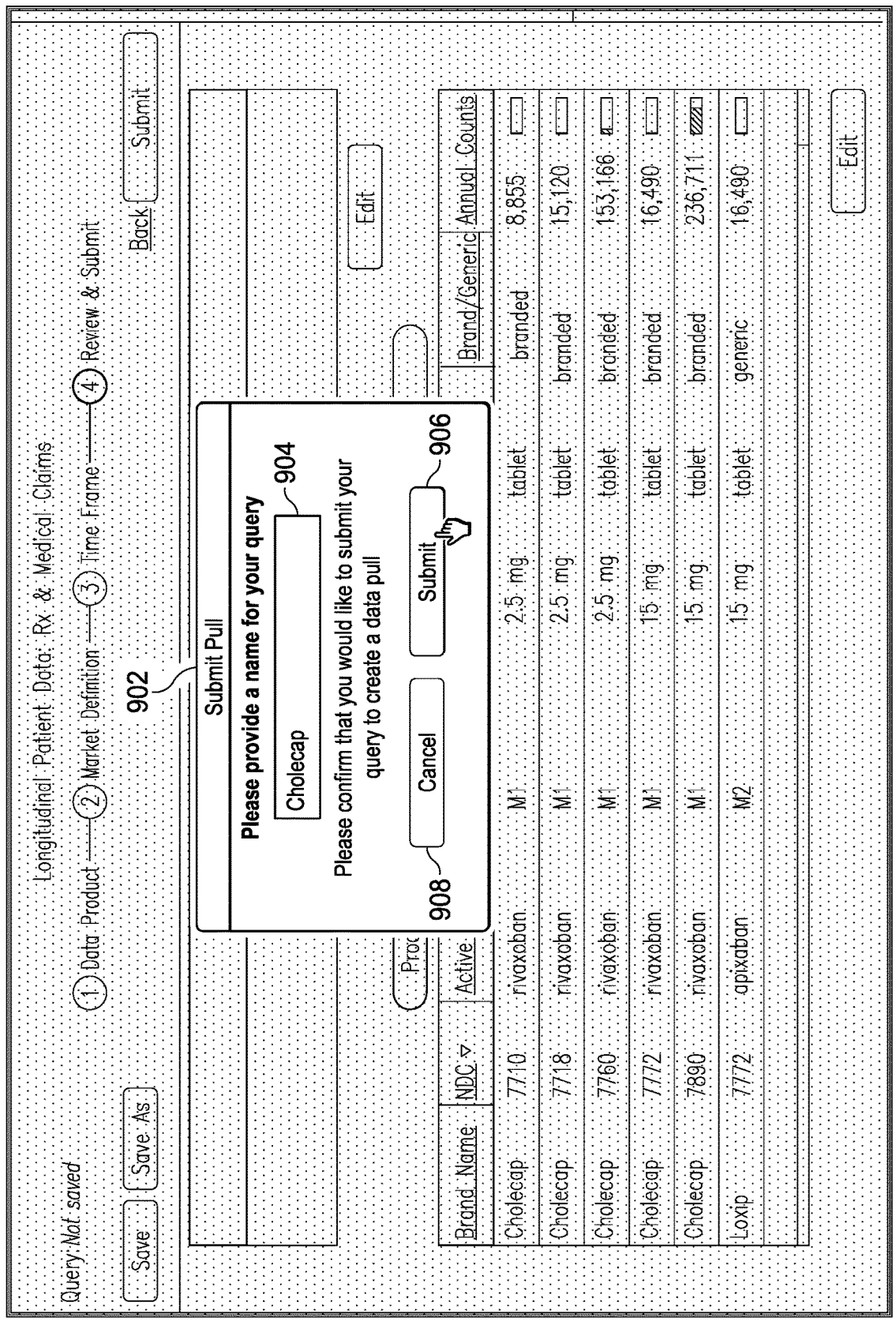
FIG. 9 shows an example interface for naming the query used in the data pull process, according to one embodiment.

FIG. 9 shows an interface 900 for naming the query used in the data pull process, according to one embodiment. Example interface 900 has transitioned to the submit and review stage 408. After all information have been entered via example interfaces 300-800, a query may be devised to perform the data pull process. Example interface 900 may include submit pull box 902 where the user may enter the name of the query in a text 904. In this case, the name of the query is Cholecap. The user may submit or cancel the query name by selecting input fields 906 or 908.

FIG. 10 shows an example interface 1000 for the job manager 420, according to one embodiment. The example interface 1000 may allow a user to view submitted jobs by selecting input field 1002 or view drafts of future jobs by selecting input field 1004 in job manager 420. Also, the example interface 1000 may include a table listing 1001 showing the details of a job. The table listing 1001 may include the following fields: Job ID 1006, Query 1008, Submitted 1010, Product 1012, Initiated By 1014, Cadence 1016, Status 1018, Completed 1020, Third Party Agreement (TPA) 1022, and Duplicate 1023. Example interface 1000 show three jobs 1024, 1026, and 1028. Two of the jobs 1026 and 1028 have been previously completed, as indicated by Completed field 1020. Moreover, jobs 1026 and 1028 include share button 1030a and 1030b under TPA field 1022. The data from completed jobs 1026 and 1028 may be shared with third parties, which will be discussed further herein. Also, the data from completed jobs 1026 and 1028 may be duplicated using duplicate button 1032a and 1032b. Job 1024 is associated with the query named "Cholecap" of FIG. 9 and is currently processing. Since job 1024 is not completed, TPA field 1022 and Duplicated 1023 are not available.

In some implementations, example interface 1000 may include more or less jobs compared to those shown in FIG. 9.

Figure 11:
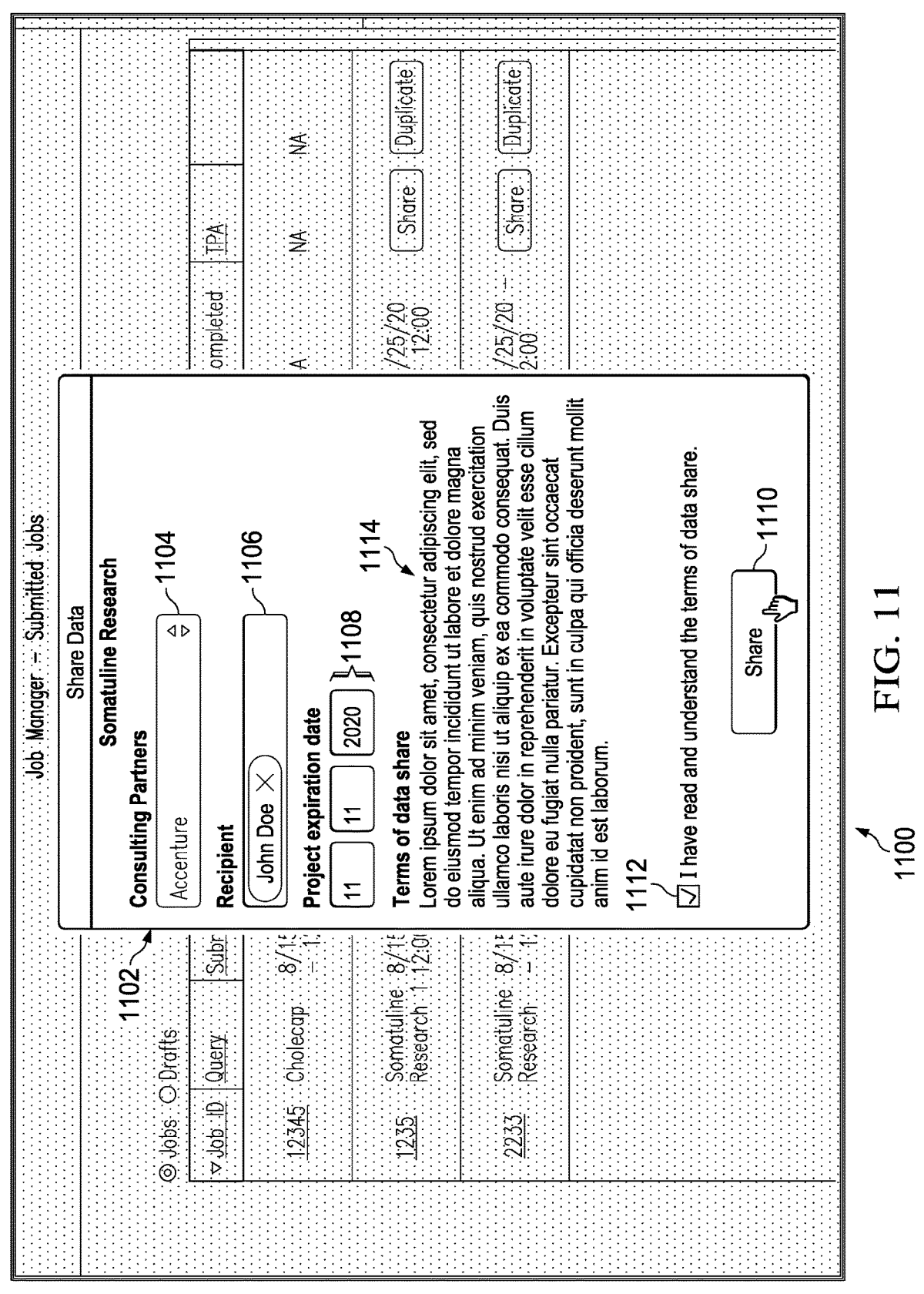

FIG. 11 shows an example interface 1100 for sharing a job with another user, according to one embodiment. When a user intends to the share a completed job, example interface 1000 shows the user may click share buttons 1030a or 1030b to initiate example interface 1100. In this case, the users intends to share completed job 1028. Example interface 1100 may include a share data input box 1102. The data input box 1102 may include a consulting partners input field 1104, recipient input field 1106, and project expiration date input field 1108. The user may input via the consulting partners input field 1104 the one or more consulting partners having access to the completed job 1028. In some implementations, the consulting partners input field 1104 may be a drop menu listing all the consulting partners.

The user may input via the recipient input field 1106 the email addresses of the one or more recipients having access to the completed job 1028. In some implementations, the one or more recipients may be associated with the user's company or network. The user may input via the recipient input field 1106 the email addresses of the one or more recipients having access to the completed job. The expiration date of access to the completed job is entered via the project expiration date input field 1108.

Once consulting partners input field 1104, recipient input field 1106, and project expiration date input field 1108 have been properly entered, a Terms of data share text box 1114 may be provided based on the one or more consulting partners and/or recipients having access to the completed job 1028. The user may click check box 1112 confirming they have read and confirmed the terms of the data share show in text box 1114. Afterwards, the user may share the completed job with the one or more consulting partners and/or recipients via button 1110.

Figure 13:
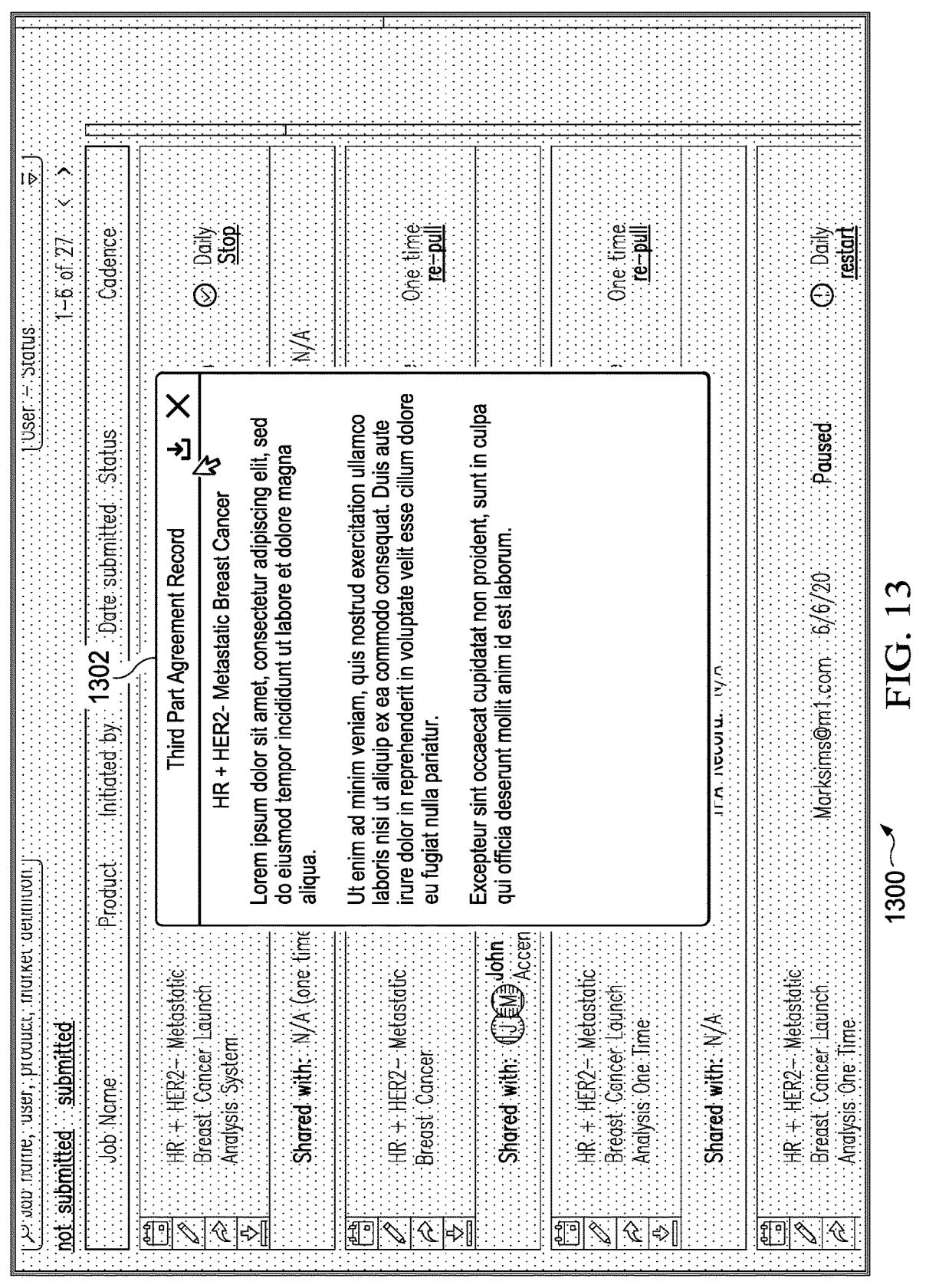

FIG. 12 shows an example interface 1200 for sharing a job with another user, according to one embodiment. Example interface 1200 is similar to example interface 1000. In this case, the jobs 1204, 1206, and 1208 are different. Job 1206 may indicate the various consulting partners and/or recipients 1210 having access to job 1206 for data sharing. Note the TPA record link 1212 may provide access to a website or directory detailing the TPA for job 1206. Example interface 1200 may allow for additional consulting partners or recipients 1210 to be added. FIG. 13 shows an example interface 1300 for displaying a TPA record 1302 once additional consulting partners or recipients 1210 are added for job 1206.

Figure 14:
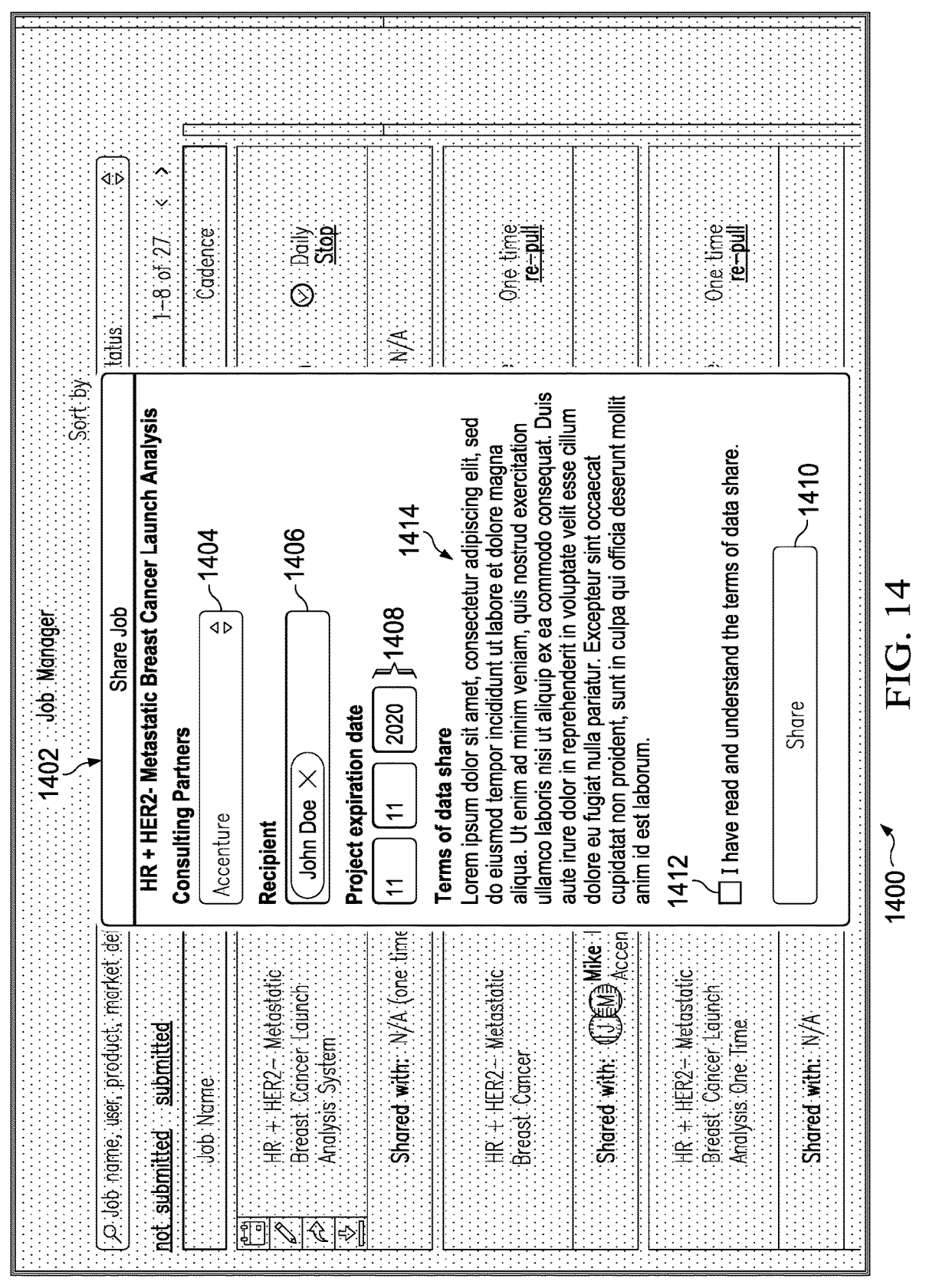

FIG. 14 shows an example interface 1400 for adding consulting partners or recipient to a previously shared job, according to one embodiment. In this case, the user intends to add new consulting partners and/or recipients to the previously shared job 1206. Example interface 1400 may include a share data input box 1402. The data input box 1402 may include a consulting partners input field 1404, recipient input field 1406, and project expiration date input field 1408. The user may input via the consulting partners input field 1404 the additional consulting partners having access to the completed job 1206. In some implementations, the consulting partners input field 1404 may be a drop menu listing all the consulting partners.

The user may input via the recipient input field 1406 the email addresses of the additional recipients having access to the completed job 1206. In some implementations, the additional recipients may be associated with the user's company or network. The expiration date of access to the completed job 1206 is entered via the project expiration date input field 1408.

Once consulting partners input field 1404, recipient input field 1406, and project expiration date input field 1408 have been entered, a Terms of data share text box 1414 may be provided based on the additional consulting partners and/or recipients having access to the completed job 1206. The user must click check box 1412 indicating they have read and confirmed the terms of the data share shown in text box 1414. Afterwards, the user may share the completed job with the additional consulting partners and/or recipients via button 1410.

FIG. 15 shows an example interface 1500 of a consulting partner or recipient receiving a request to access data of a completed job, according to one embodiment. The example interface 1500 may include a table listing 1501 defining the existing shared jobs 1516, 1518. The table listing 1501 may include the following fields: job name 1502, Product 1504, Shared by 1506, Date shared 1508, and Expires on 1510. In this case, shared job 1516 may be awaiting the consulting partner or recipient to accept or decline the pending share job 1516. If the consulting partner or recipient accepts the pending shared job 1516, they will have access to the data to the data of job 1516. Text box 1512 may allow a user to search for a particular shared job by name, user product, or market definition. Drop down menu 1514 may permit a user sort the table listing 1501 in accordance with the fields 1502-1510.

Figure 16:
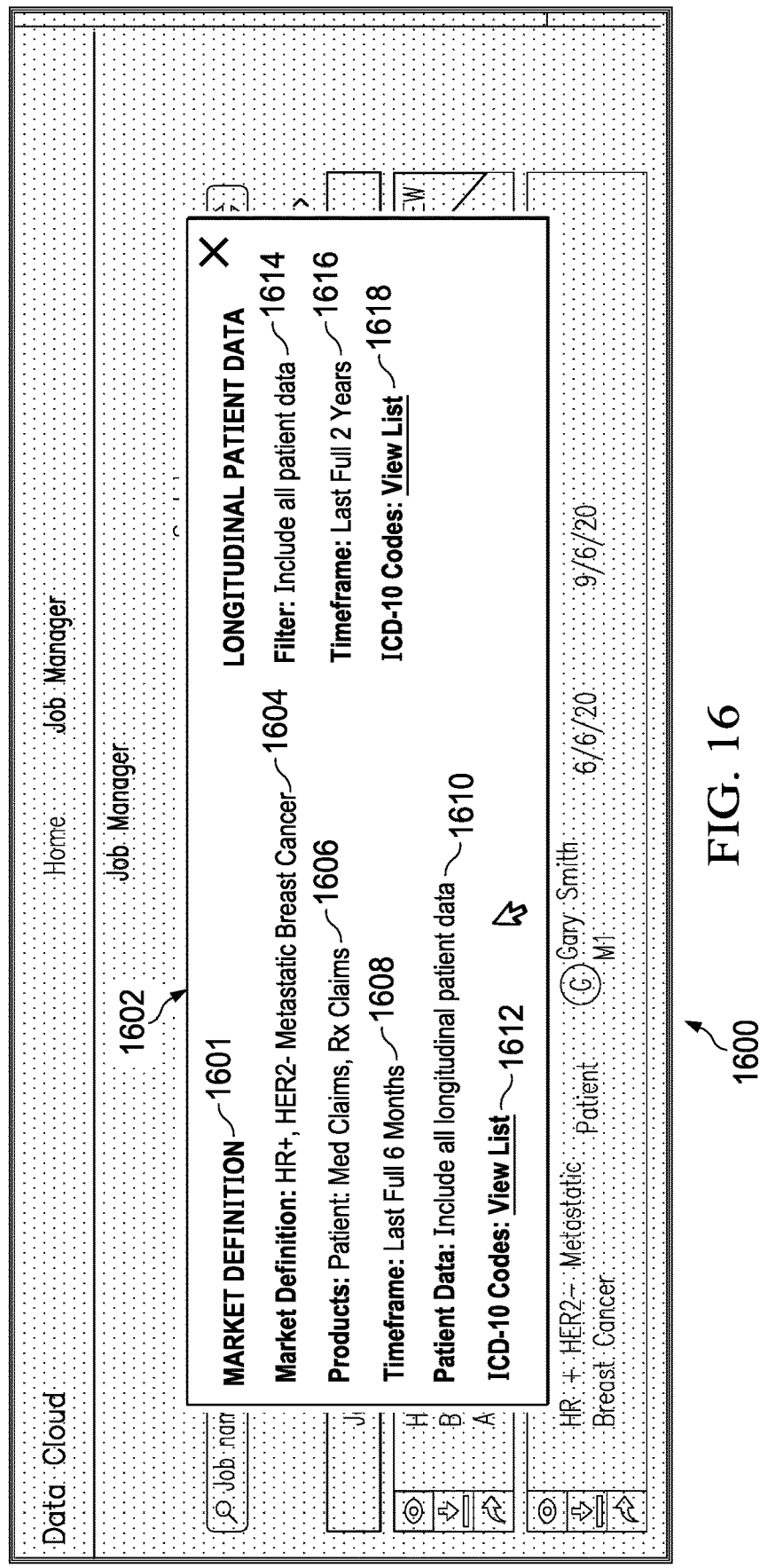
FIG. 16 shows an example interface for displaying information regarding shared data, according to one embodiment.

FIG. 16 shows an example interface 1600 for displaying information regarding the shared data, according to one embodiment. After accepting shared job 1516, example interface 1600 may be initiated to provide the consulting partner or recipient information regarding the underlying data of shared job 1516. The example interface 1600 may include a status box 1602 indicating the parameters defining the market definition 1601 and longitudinal patient data 1603 used in the data pull process for shared job 1516. The market definition 1601 may include a market definition parameter 1604, Product parameter 1606, timeframe parameter 1608, patient data parameter 1610, and ICD-10 Codes parameter 1612. The longitudinal patient data 1603 may include a filter parameter 1614, a timeframe 1616, and a ICD-10 Codes parameter 1618. Note the market definition 1601 and longitudinal patient data 1603 may be entered using the example interfaces of FIGS. 3-8.

FIG. 17 shows an example interface 1700 for allowing a user of share data to change specific properties of the data of a shared job, according to one embodiment. Using shared job 1516 of FIG. 15, example interface 1700 may allow a consulting partner or recipient to change attribute of the underlying shared data for processing. The example interface 1700 may allow a user to select the use case of the shared data. In this instance, the use case may include patient journey information 1702, targeting information 1704, market access information 1706, HEOR information 1708, segmentation 1710, and medical affairs information 1712. Moreover, a user may select data attributes and outputs based on use-case driven data enabling users to get to the insights they need faster from a smaller dataset.

The example interface 1700 may include a table listing 1701 having the following fields: Data File 1720; select all attribute 1722, Category 1724, Attribute 1722, individual attributes 1728, and Example Data 1742. The Data File field 1720 may be associated with various data files 1730, 1732, and 1734 used in data pull process for share job 1516. Data file 1730 may have a number attributes 1736a . . . 1736f group by the Category field 1724. In this case, the user selects all the attributes of the Core category 1736a as indicated by the attribute field 1722. The example interface 1700 may allow a user to select a few of its attributes by clicking its corresponding individual attributes field 1724. Also, a user may configure the specific attributes and aggregations of fields 1720-1734 to be delivered as part of an output schema.

Moreover, Data file 1732 may have a number attributes 1738a . . . 1738f group by the Category field 1724. In this case, the user selects all the attributes of the Core category 1738a as indicated by the attribute field 1722. The example interface 1700 may allow a user to select a few of its attributes by clicking its corresponding individual attributes field 1724 for data file 1732. Data file 1732 may have a number attributes 1738a . . . 1738c group by the Category field 1724. In this case, the user selects all the attributes of the Core category 1738a as indicated by the attribute field 1722. The example interface 1700 may allow a user to select a few of its attributes by clicking its corresponding individual attributes field 1724 for data file 1732. Furthermore, the example interface 1700 may allow a user to select a few of its attributes by clicking its corresponding individual attributes field 1724 for data file 1734. Data file 1734 may have a number attributes 1740a . . . 1740c grouped by the Category field 1724. The user selects all the attributes of the Core category 1740a as indicated by the attribute field 1722. The example interface 1700 may allow a user to select a few of its attributes by clicking its corresponding individual attributes field 1724 for data file 1734.

Input fields 1714, 1716, and 1718 may allow a user to select all attributes defined for each data file 1730, 1732, 1734, select of none of the listed attributes for each data file 1730, 1732, 1734, or only those attribute selected by the user of the share data. Once all information have been properly entered for example interface 1700, the user may press button 1744 to continue processing.

FIG. 18 shows an example interface 1800 for allowing a user of shared data to change target location and information of the shared data for analysis, according to one embodiment. Using shared job 1516 of FIG. 15, example interface

1800 may permit a shared data user to devise new data sets using the underlying data of share job 1516 in a new pull process. The example interface 1800 may include a table listing 1801 including the following fields: Job Name 1802, Target File Name 1804, Data Product 1806, Initiated 1808, Completed 1810, and Pull Status 1812. The Job Name Field 1802 may include the same job name as shared job 1516. The new data set may have a new job name as shown by Target File Name field 1804. The Data Product field 1806 may identity a product of interest in the new data set. The Initiated field 1808 may indicate when a new data set has been initiated and the Completed Field 1810 may indicate when the pull process for the new data set was completed and ready for use.

The Pull Status field 1812 may show data pull status for the new data set, which in this case is a one-time data pull process. In some implementations, Pull Status field 1812 may show the term "Unlimited" indicating the shared data user may initiate an unlimited number of data pulls to devise new data sets. Table listing 1801 may include a Market Definition field detailing the market definition parameters 1832a . . . 1832d. Each of the market definition parameters 1832a . . . 1832d may include a corresponding edit button 1818. The edit button 1818 may allow a shared data user to access the example interfaces 500, 600, 700, and 800 to adjust the various market definition parameters 1832a . . . 1832d.

Moreover, table listing 1801 may include a Longitudinal Patient Data field 1816 detailing the Longitudinal Patient Data parameters 1834a-1834b. Each of the Longitudinal Patient Data parameters 1834a-1834b may include a corresponding edit button 1820a-1820b. The edit button 1820a or 1820b may allow a shared data user to access the example interfaces 500, 600, 700, and 800 to adjust the various market definition parameters Longitudinal Patient Data parameters 1834a-1834b. Also, table listing 1801 may include an Attribute field 1817 detailing a link 1824 marked "previous." The "previous" link 1824 may provide access to example interface 1700 showing the current attributes of job 1516. Attribute field 1817 may include an edit button 1822 allowing for a shared data user to edit the attributes using example interface 1500.

Once all required data is entered in example interface 1800, the shared data user may download the new data set with button 1826, schedule a data stream for the new data set using button 1828, or edit the shared data request using button 1830. If the shared data user downloads the new data set via button 1826, pop-up window 1840 may appear requesting the shared data user to specify where to download the new data set having the target file name specified by field 1804. Moreover, a user may configure their own and choose an exchange protocol of their choice, such as SFTP, S3, or local machine.

In some implementations, users may schedule data to be delivered with their set configuration on an ongoing schedule or cadence. Users may choose one time, monthly, or daily level data pulls using button 1828.

Figure 19:
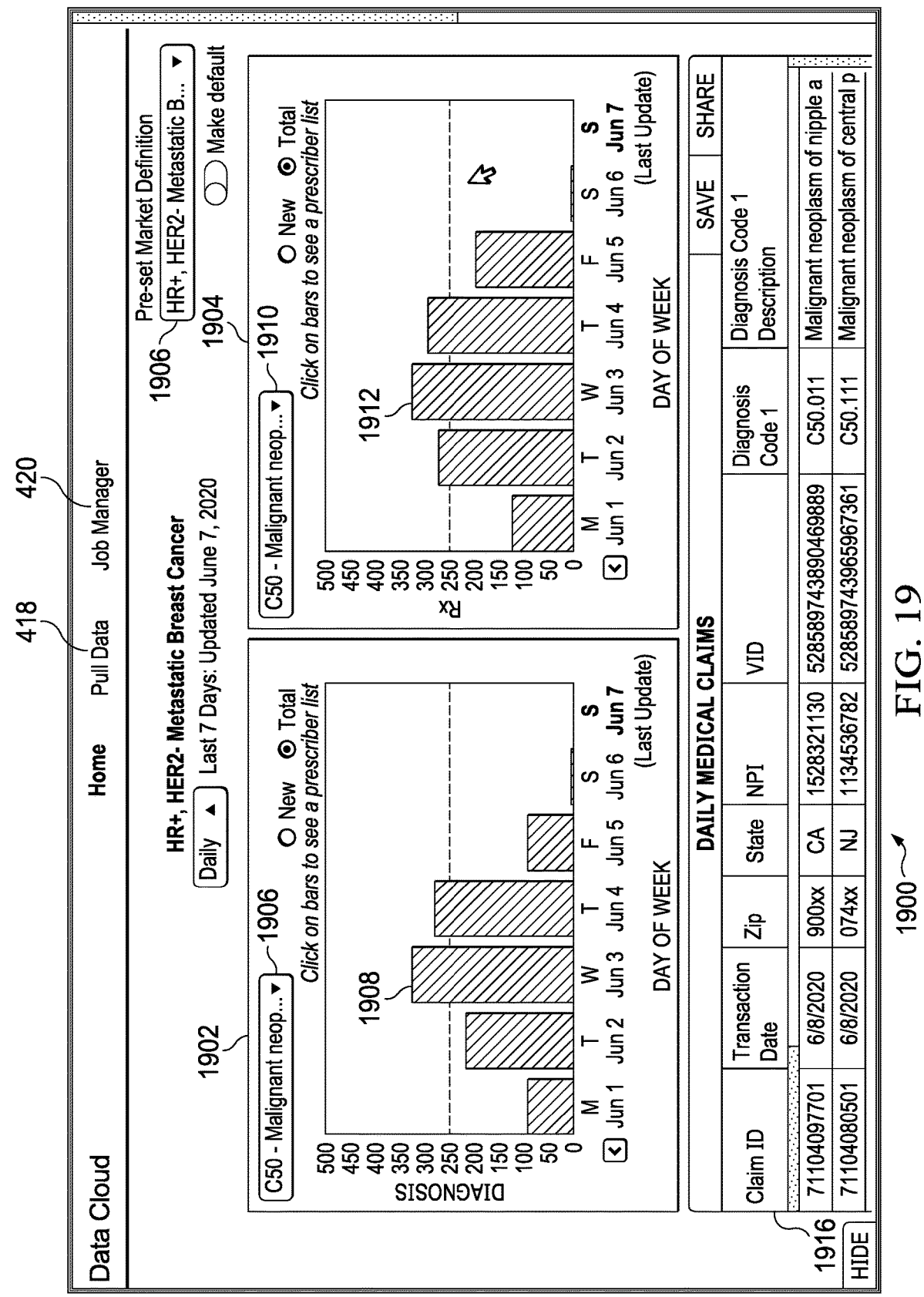
FIG. 19 shows an example interface for providing insights on the data provided, according to one embodiment.

FIG. 19 shows an example interface 1900 for providing insights on the data provided, according to one embodiment. The user may select the data by referencing drop-down menu 1914. The drop-down menu 1914 may include a listing of all the completed jobs whose data are available. The example interface 1900 may include two visual boxes 1902 and 1904. The visual box 1902 may include a drop-down menu 1906 providing a listing of all diagnosis, which a user may select. Histogram 1908 may be displayed in the visual box 1902 referencing daily data associated with the diagnosis shown in drop-down menu 1906. The visual box 1904 may include a drop-down menu 1910 providing a listing of all products, which a user may select. Histogram 1912 may be displayed in the visual box 1904 referencing daily data associated with the diagnosis shown in drop-down menu 1910. Table listing 1916 may include a listing of the data used to devise histograms 1902 and 1904. Drop-down button 1918 may a listing of available timeframes used for preparing the user insights, which in this case is daily. The available timeframes may be based on the data provided.

In some embodiments, the available timeframes may be weekly, monthly, or a preset timeframe selected by a user as supported by the underlying data. In some embodiments, a user may set custom, pre-configured market definitions to be used for queries across products listed in drop-down menu 1906. In some embodiments, example interface 1900 may enable configurable data visualizations, trend monitoring, and data exploration.

Figure 20:
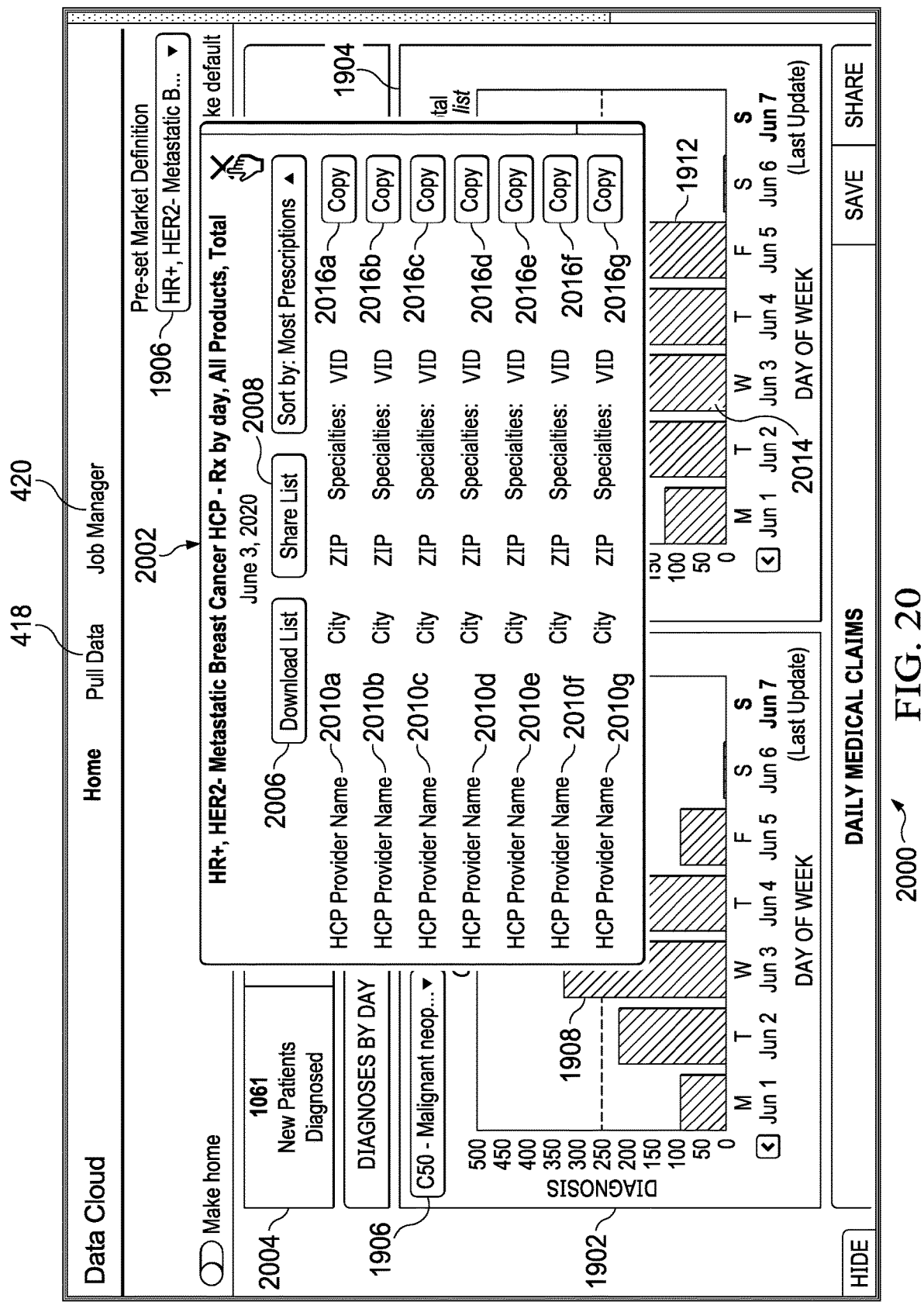
FIG. 20 shows an example interface for providing detailed information on content shown in the example interface of FIG. 19, according to one embodiment.

FIG. 20 shows an example interface 2000 for providing detailed information on content shown in example interface 1900, according to one embodiment. The example interface 2000 is similar to example interface 1900 of FIG. 19. Example interface 2000 may further include a visual box 2002 that is activated when a user clicks one of the bins of the histogram 1908 or 1912. In this instance, bin 2014 was clicked by the user. The visual box 2002 may list a number of data elements 2010a . . . 2010h defining the clicked bin 2014. Also, the visual box 2002 may include a download list button 2006 allowing a user to download the data elements 2010a . . . 2010h for further analysis. Moreover, the visual box 2002 may include a share list button 2008 for sharing the data elements 2010a . . . 2010h with one or more consulting parties or recipients using the same approaches discussed for example interfaces 1000 and 1100 of FIGS. 10 and 11. The data of each data element 2010a . . . 2010h may be individually copied using copy buttons 2016a . . . 2016h. Moreover, the data elements 2010a . . . 2010h may be sorted using drop-down button 2012. The drop-down button 2012 may include a listing of elements for sorting the data elements 2010a . . . 2010h. The example interface 2000 may include an information table 2004 indicating key information regarding the data elements 2016a . . . 2016h of the clicked bin 2014.

Workflow

FIGS. 21A-21B show flowcharts 2100 illustrating a method for managing and accessing data using one or more data cloud servers 105, according to one embodiment. In block 2102, the method includes receiving an initial request for accessing data. At block 2104, the method includes determining one or more external sources to retrieve the data. At block 2106, the method includes receiving a first request for a first configuration data set having a first set of configuration properties. At block 2108, the method includes retrieving, using the one or more computing device processors, the first configuration data set from the one or more external sources.

At block 2110, the method includes initiating display of the first configuration data set including the first set of configuration properties. The method includes receiving selection of one or more elements of the first configuration data set to form a first select configuration data set, as shown at block 2112. Also, the method includes receiving a second request for a second configuration data set having a second set of configuration properties, as shown at block 2114. At block 2116, the method includes retrieving the second configuration data set from the one or more external sources.

At block 2118, the method includes initiating display of the second configuration data set including the second set of configuration properties. Moreover, the method includes receiving selection of one or more elements of the second configuration data set to form a second select configuration data set, as shown at block 2120. Also, the method includes receiving a third request for a third configuration data set having a third set of configuration properties, as shown at block 2122. At block 2124, the method includes retrieving the third configuration data set from the one or more external sources.

At block 2126, the method includes initiating display of the third configuration data set including the third set of configuration properties. The method includes receiving selection of one or more elements of the third configuration data set to form a third select configuration data set, as shown at block 2128. Moreover, the method includes determining a timeframe for retrieving data associated with at least one of the first select configuration data set, the second select configuration data set, and the third select configuration data set, as shown at block 2130. At block 2132, the method includes generating a query based on data associated with the timeframe, the at least one of the first select configuration data set, the second select configuration data set, and the third select configuration data set, or other data related to the at least one of the first select configuration data set, the second select configuration data set, and the third select configuration data set.

In some implementations, the data cloud server 105 may parse and execute the query including retrieving from the one or more external sources output data. In other implementations, the output data may be formed in accordance with the timeframe associated with the first select configuration data set, the second select configuration data set, or the third select configuration data set. In some implementations, query format may be compatible with the data cloud server 105. In some implementations, the data cloud server 105 reformats the query in a format compatible with the one or more external sources to retrieve information.

At block 2134, the method includes executing the query according to a cadence. At block 2136, the method includes retrieving from the one or more external sources, output data. The method includes receiving a first instruction from the user to provide access to the output data to a first set of one or more recipient systems, as shown at block 2138. Moreover, in response to receiving the first instruction from the user to provide access to the output data, the method includes sending to the first set of the one or more recipient systems, one or more exchange protocols for accessing the output data, as shown at block 2140.

At block 2142, the method includes receiving acceptance of the one or more exchange protocols from the first set of the one or more recipient systems for access to the output data. In response to receiving the acceptance of the one or more exchange protocols from the first set of the one or more recipient systems, method includes providing the first set of the one or more recipient systems with access to the output data, otherwise the output data is blocked from the first set of the recipient systems, as shown at block 2144. Moreover, the method includes receiving a second instruction from the first set of the one or more recipient systems to provide access to the output data to a second set of the one or more recipient systems, as shown at block 2146. In response to receiving the second instruction from the first set of the one or more recipient systems to provide access to the output data, the method includes sending to the second set of the one or more recipient systems, the one or more exchange protocols or second one or more exchange protocols for accessing the output data, as shown at block 2148.

At block 2150, the method includes receiving acceptance of the one or more exchange protocols or the second one or more exchange protocols from the second set of the one or more recipient systems for accessing the output data. In response to receiving the acceptance of the one or more exchange protocols or the second one or more exchange protocols from the second set of the one or more recipient systems, the method includes providing the second set of the one or more recipient systems with access to the output data, otherwise the output data is blocked from the second set of the recipient systems, as shown at block 2152.

In some implementations, the user may initiate a data pull process for accessing data by engaging with the example interface 300.

In other implementations, the user may select the one or more external sources using the example interface 400.

In some implementation, the first configuration data set may the search results of table listing 511 for a specific product, such as Cholecap. In some implementations, the first set of configuration properties may be any of the fields 510, 512, 514, 516, 518, 520, 522, and 524 of table listing 511, as shown in FIG. 5.

In some implementations, the second configuration data set may the search results of table listing 711 for a specific diagnosis, such as heart disease. In some implementations, the second set of configuration properties may be any of the fields 708, 710, 712, 714, and 716 of table listing 711, as shown in FIG. 7.

In some implementations, the third configuration data set may be search results of a table listing of specific procedures discussed for the Added Procedure selection window 532. In some implementations, the second set of configuration properties may be any of the fields of the table listing discussed for Added Procedure selection window 532.

In some embodiments, the timeframe may be entered by the user for each of the first select configuration data set, the second select configuration data set, and/or the third select configuration data set using example interface 800.

In some implementations, the one or more first or second recipient systems may be the consulting partners and/or recipients 1104. In some implementations, user example interface 1100 may send a message to the data cloud server 105 that the first set of the one or more recipient systems have accepted the one or more third party agreements. In some implementations, user example interface 1100 may receive notification from data cloud server 105 of the receipt of acceptance of the one or more third party agreements by the first set of the one or more recipient systems. In some implementation, data cloud server 105 may analyze the second instruction to determine the network address of the second set of the one or more recipient systems and if the network address of the second set of the one or more recipient systems are different from the network address of the user and the first set of the one or more recipient systems.

Reference in the specification to "one implementation" or "an implementation" means that a particular feature, structure, or characteristic described in connection with the implementation is included in at least one implementation of the disclosure. The appearances of the phrase "in one implementation," "in some implementations," "in one instance," "in some instances," "in one case," "in some cases," "in one embodiment," or "in some embodiments" in various places in the specification are not necessarily all referring to the same implementation or embodiment. In some embodiments, the terms "signal," "data," and/or "information" may be used interchangeably. In some embodiments, signals refer to non-transitory signals.

Finally, the above descriptions of the implementations of the present disclosure have been presented for the purposes of illustration and description. It is not intended to be exhaustive or to limit the present disclosure to the precise form disclosed. Many modifications and variations are possible in light of the above teaching. It is intended that the scope of the present disclosure be limited not by this detailed description, but rather by the claims of this application. As will be understood by those familiar with the art, the present disclosure may be embodied in other specific forms without departing from the spirit or essential characteristics thereof. Accordingly, the present disclosure is intended to be illustrative, but not limiting, of the scope of the present disclosure, which is set forth in the following claims.

What is claimed is:

1. A method for managing and accessing data using one or more data cloud servers, the method comprising:
receiving, using one or more computing device processors, an initial request for accessing data;
determining, using the one or more computing device processors, one or more external sources to retrieve the data;
receiving, using the one or more computing device processors, a first request for a first configuration data set having a first set of configuration properties;
retrieving, using the one or more computing device processors, the first configuration data set from the one or more external sources;
initiating display of, using the one or more computing device processors, the first configuration data set including the first set of configuration properties;
receiving selection of, using the one or more computing device processors, one or more elements of the first configuration data set to form a first select configuration data set;
receiving, using the one or more computing device processors, a second request for a second configuration data set having a second set of configuration properties;
retrieving, using the one or more computing device processors, the second configuration data set from the one or more external sources;
initiating display of, using the one or more computing device processors, the second configuration data set including the second set of configuration properties;
receiving selection of, using the one or more computing device processors, one or more elements of the second configuration data set to form a second select configuration data set;
receiving, using the one or more computing device processors, a third request for a third configuration data set having a third set of configuration properties;
retrieving, using the one or more computing device processors, the third configuration data set from the one or more external sources;
initiating display of, using the one or more computing device processors, the third configuration data set including the third set of configuration properties;
receiving selection of, using the one or more computing device processors, one or more elements of the third configuration data set to form a third select configuration data set;
determining, using the one or more computing device processors, a timeframe for retrieving data associated with at least one of the first select configuration data set, the second select configuration data set, and the third select configuration data set;
generating, using the one or more computing device processors, a query based on data associated with the timeframe, the at least one of the first select configuration data set, the second select configuration data set, and the third select configuration data set, or other data related to the at least one of the first select configuration data set, the second select configuration data set, and the third select configuration data set;
executing, using the one or more computing device processors, the query according to a cadence;
retrieving, using the one or more computing device processors, from the one or more external sources, output data;
receiving, using the one or more computing device processors, a first instruction from a user to provide access to the output data to a first set of one or more recipient systems;
in response to receiving the first instruction from the user to provide access to the output data, sending, using the one or more computing device processors, to the first set of the one or more recipient systems, one or more exchange protocols for accessing the output data;
receiving, using the one or more computing device processors, acceptance of the one or more exchange protocols from the first set of the one or more recipient systems for access to the output data;
in response to receiving the acceptance of the one or more exchange protocols from the first set of the one or more recipient systems, providing, using the one or more computing device processors, the first set of the one or more recipient systems with access to the output data, otherwise the output data is blocked from the first set of the recipient systems;
receiving, using the one or more computing device processors, a second instruction from the first set of the one or more recipient systems to provide access to the output data to a second set of the one or more recipient systems;
in response to receiving the second instruction from the first set of the one or more recipient systems to provide access to the output data, sending, using the one or more computing device processors, to the second set of the one or more recipient systems, the one or more exchange protocols or second one or more exchange protocols for accessing the output data;
receiving, using the one or more computing device processors, acceptance of the one or more exchange protocols or the second one or more exchange protocols from the second set of the one or more recipient systems for accessing the output data; and
in response to receiving the acceptance of the one or more exchange protocols or the second one or more exchange protocols from the second set of the one or more recipient systems, providing, using the one or more computing device processors, the second set of the one or more recipient systems with access to the output data, otherwise the output data is blocked from the second set of the recipient systems.

2. The method of claim 1, wherein receiving the initial request for accessing the data comprises receiving the initial request via a user interface executing on a computing device processor different from the one or more computing device processors.

3. The method of claim 2, wherein determining the one or more external sources to retrieve the data comprises receiving an indication from the user which of the one or more external sources are used for retrieving the data.

4. The method of claim 1, wherein determining the timeframe for retrieving the data associated with the at least one of the first select configuration data set, the second select configuration data set, and the third select configuration data set comprises receiving the timeframe for retrieving the data associated with the at least one of the first select configuration data set, the second select configuration data set, and the third select configuration data set from the user.

5. The method of claim 1, wherein executing the query comprises parsing the query to determine which of the one or more external sources are used to retrieve the output data.

6. The method of claim 5, further comprising generating one or more new queries to be sent to the one or more external sources for retrieving the output data.

7. The method of claim 1, wherein receiving the first instruction from the user to provide access to the output data comprises analyzing the first instruction to determine a network address of the first set of the one or more recipient systems.

8. The method of claim 1, wherein sending to the first set of the one or more recipient systems the one or more exchange protocols comprises initiating display of the one or more exchange protocols to the first set of the one or more recipient systems.

9. The method of claim 8, wherein receiving the acceptance of the one or more exchange protocols comprises notifying the user of the acceptance of the one or more exchange protocols by the first set of the one or more recipient systems via a user interface.

10. The method of claim 1, wherein receiving the second instruction from the first set of the one or more recipient systems to provide access to the output data comprises analyzing the second instruction to determine a network address of the second set of the one or more recipient systems and if the network address of the second set of the one or more recipient systems is different from a network address of the user and a network address of the first set of the one or more recipient systems.

11. A system for managing and accessing data using one or more data cloud servers, the system comprising:
one or more computing device processors; and
one or more computing device memories, coupled to the one or more computing device processors, the one or more computing device memories storing instructions executed by the one or more computing device processors, wherein the instructions are configured to:
receive an initial request for accessing data;
determine one or more external sources to retrieve the data;
receive a first request for a first configuration data set having a first set of configuration properties;
retrieve the first configuration data set from the one or more external sources;
initiate display of the first configuration data set including the first set of configuration properties;
receive selection of one or more elements of the first configuration data set to form a first select configuration data set;
receive a second request for a second configuration data set having a second set of configuration properties;
retrieve the second configuration data set from the one or more external sources;
initiate display of the second configuration data set including the second set of configuration properties;
receive selection of one or more elements of the second configuration data set to form a second select configuration data set;
receive a third request for a third configuration data set having a third set of configuration properties;
retrieve the third configuration data set from the one or more external sources;
initiate display of the third configuration data set including the third set of configuration properties;
receive selection of one or more elements of the third configuration data set to form a third select configuration data set;
determine a timeframe for retrieving data associated with at least one of the first select configuration data set, the second select configuration data set, and the third select configuration data set;
generate a query based on data associated with the timeframe, the at least one of the first select configuration data set, the second select configuration data set, and the third select configuration data set, or other data related to the at least one of the first select configuration data set, the second select configuration data set, and the third select configuration data set;
execute the query according to a cadence;
retrieve from the one or more external sources, output data;
receive a first instruction from a user to provide access to the output data to a first set of one or more recipient systems;
in response to receiving the first instruction from the user to provide access to the output data, send to the first set of the one or more recipient systems, one or more exchange protocols for accessing the output data;
receive acceptance of the one or more exchange protocols from the first set of the one or more recipient systems for access to the output data;
in response to receiving the acceptance of the one or more exchange protocols from the first set of the one or more recipient systems, provide the first set of the one or more recipient systems with access to the output data, otherwise the output data is blocked from the first set of the recipient systems;
receive a second instruction from the first set of the one or more recipient systems to provide access to the output data to a second set of the one or more recipient systems;
in response to receiving the second instruction from the first set of the one or more recipient systems to provide access to the output data, send to the second set of the one or more recipient systems, the one or more exchange protocols or second one or more exchange protocols for accessing the output data;
receive acceptance of the one or more exchange protocols or the second one or more exchange protocols from the second set of the one or more recipient systems for accessing the output data; and
in response to receiving the acceptance of the one or more exchange protocols or the second one or more exchange protocols from the second set of the one or more recipient systems, provide the second set of the one or more recipient systems with access to the output data, otherwise the output data is blocked from the second set of the recipient systems.

12. The system of claim 11, wherein the instructions are further configured to provide a user interface for allowing the user to select which of the one or more external sources to retrieve data.

13. The system of claim 11, wherein the instructions are further configured to provide a user interface for displaying details of the at least one of the first set of configuration properties, the second set of configuration properties, and the third set of configuration properties.

14. The system of claim 11, wherein the instructions are further configured to provide a user interface for selecting at least one of the one or more elements of the first configuration data set, the one or more elements of the second configuration data set, and the one or more elements of the third configuration data set.

15. The system of claim 11, wherein the instructions are further configured to provide a user interface for displaying the one or more elements of the first configuration data set, the one or more elements of the second configuration data set, and the one or more elements of the third configuration data set based on one or more user criteria.

16. The system of claim 11, wherein the instructions are further configured to provide a user interface for indicating when the output data is available for sharing with the first set of the one or more recipient systems or the second set of the one or more recipient systems.

17. The system of claim 11, wherein the instructions are further configured to provide a user interface for indicating the first set of the one or more recipient systems or the second set of the one or more recipient systems sharing the output data.

18. A method for managing and accessing data using one or more data cloud servers, the method comprising:
receiving, using one or more computing device processors, a first request for accessing data;
determining, using the one or more computing device processors, one or more external sources to retrieve the data;
retrieving, using the one or more computing device processors, an at least first configuration data set from the one or more external sources, wherein the at least first configuration data set has an at least first set of configuration properties;
initiating display of, using the one or more computing device processors, the at least first configuration data set including the at least first set of configuration properties;
receiving selection of, using the one or more computing device processors, one or more elements of the at least first configuration data set to form an at least first select configuration data set;
determining, using the one or more computing device processors, a timeframe for retrieving data associated with the at least first select configuration data set;
generating, using the one or more computing device processors, a query based on data associated with the timeframe, the at least first select configuration data set, or other data related to the at least first select configuration data set;
executing, using the one or more computing device processors, the query according to a cadence;
retrieving, using the one or more computing device processors, from the one or more external sources, output data;
receiving, using the one or more computing device processors, a first instruction from a user to provide access to the output data to a first set of one or more recipient systems;
in response to receiving the first instruction from the user to provide access to the output data, sending, using the one or more computing device processors, to the first set of the one or more recipient systems, one or more exchange protocols for accessing the output data;
receiving, using the one or more computing device processors, acceptance of the one or more exchange protocols from the first set of the one or more recipient systems for access to the output data;
in response to receiving the acceptance of the one or more exchange protocols from the first set of the one or more recipient systems, providing, using the one or more computing device processors, the first set of the one or more recipient systems with access to the output data;
receiving, using the one or more computing device processors, a second instruction from the first set of the one or more recipient systems to provide access to the output data to a second set of the one or more recipient systems;
in response to receiving the second instruction from the first set of the one or more recipient systems to provide access to the output data, sending, using the one or more computing device processors, to the second set of the one or more recipient systems, the one or more exchange protocols or second one or more exchange protocols for accessing the output data;
receiving, using the one or more computing device processors, acceptance of the one or more exchange protocols or the second one or more exchange protocols from the second set of the one or more recipient systems for accessing the output data; and
in response to receiving the acceptance of the one or more exchange protocols or the second one or more exchange protocols from the second set of the one or more recipient systems, providing, using the one or more computing device processors, the second set of the one or more recipient systems with access to the output data.

19. The method of claim 18, further comprising initiating display of a visual representation of the output data using one or more analytical tools.

20. The method of claim 19, wherein initiating display of the visual representation of the output data comprises utilizing at least one histogram to visually represent the output data.

* * * * *